US006953686B1

(12) United States Patent
Ramasubramanyan

(10) Patent No.: US 6,953,686 B1
(45) Date of Patent: Oct. 11, 2005

(54) METHODS OF DNA PURIFICATION AND PURIFIED DNA

(75) Inventor: Natarajan Ramasubramanyan, Baltimore, MD (US)

(73) Assignee: Cambrex Bio Science Baltimore, Inc., Baltimore, MD (US)

( * ) Notice: Subject to any disclaimer, the term of this patent is extended or adjusted under 35 U.S.C. 154(b) by 0 days.

(21) Appl. No.: 09/578,507

(22) Filed: May 26, 2000

Related U.S. Application Data

(60) Provisional application No. 60/136,772, filed on May 28, 1999.

(51) Int. Cl.$^7$ ............................................. C12M 1/34
(52) U.S. Cl. ................................. 435/288.6; 536/23.1
(58) Field of Search ................... 435/288.6, 6; 536/23.1

(56) References Cited

U.S. PATENT DOCUMENTS

| | | | | |
|---|---|---|---|---|
| 6,197,553 | B1 * | 3/2001 | Lee et al. | 435/91.1 |
| 6,214,586 | B1 * | 4/2001 | McNeilly | 435/91.1 |
| 6,265,168 | B1 * | 7/2001 | Gjerde et al. | 435/6 |
| 6,441,160 | B2 * | 8/2002 | Kitamura et al. | 536/25.4 |
| 2001/0034435 | A1 * | 10/2001 | Nochumson et al. | 536/23.1 |

FOREIGN PATENT DOCUMENTS

EP        0 964 057       12/1999

OTHER PUBLICATIONS

Prazeres et al. Preparative purification of supercoiled plamsid DNA using anion–exchange chromatography, J. Chromatography. vol. 806:31–45, 1998.*
Ishida et al. Chromatographic removal of endotoxin from a macromolecular intitumor antibiotic SN–07. Kagaku Kogaku Rondunshu vol. 17(3):589–594, 1991.*
Maitra et al. Properties of binding of *Escherichia coli* endotoxin to various matrices. J. Clin Microbiol. vol. 13(1):49–53, Jan. 1981.*
Colote et al. Analysis and purificatoin of plasmid DNA by reversed–phase high–performance liquid chromatography. Analytical Biochem. vol. 154:15–20, 1986.*
Kapp et al. Preparation of DNA topoisomers by RP–18 high–performance liquid chromatography. Anal. Biochem. vol. 206:293–299, 1992.*
Saha et al, "A new method of plasmid DNA . . . ", Anal Biochem Feb. 1, 1989;176(2):344–9.
Ranhand, "The enrichment of plasmid DNAs, . . . ", Prep Biochem 1985;15(3):121–31.
Sayers et al, "Identification and eradication . . . ", Anal Biochem Oct. 15, 1996;241(2):186–9.
Cooke et al, "Purification of essentially RNA free . . . ", J Biotechnol Feb. 23, 2001;85(3):297–304.
O'Kennedy et al, "Effects of growth medium selection . . . ", J Biotechnol Jan. 21, 2000;76(2–3):175–83.

Smith et al, "Fast and accurate method . . . ", Biotechniques Mar. 1999;26(3):518–22, 524, 526.
Chicz et al, "Microenvironmental contributions . . . ", J Chromatogr Feb. 2, 1990;500:503–18.
Smith et al, "Effect of stationary and mobile phases . . . ", J Chromatogr Nov. 10, 1989;496(1):71–82.
Fausnaugh et al, "Comparison of hydrophobic–interaction . . . ", J Chromatogr Dec. 28, 1984;317–:141–55.
Alpert, "Hydrophobic interaction chromatography . . . ", J Chromatogr Jul. 1, 1988;444:269–74.
Amersham Pharmacia Biosciences Catalog 2001 pp. 644 and 650.
"Reversed–Phase and Hydrophobic Interaction Chromatography of Peptides and Proteins", El Rassi et al, Yale University, New Haven, CT, pp. 447–494, in Separation Processes in Biotechnology, edited by Juan A. Asenjo, 1990. –Full Article Submitted.
Edwardson et al, "A new rapid procedure for the prparation of plasmid DNA", Anal Biochem Feb. 1, 1986;152(2):215–20.
Diogo et al, "Purification of a cystic fibrosis plasmid vector for gene therapy using hydrophobic interaction chromatography", Biotchnol Bioeng Jun. 5, 2000;68(5):576–83, abstract only.
Chaturvedi et al, "The delta–endotoxin proteins accumulate in *Escherichia coli* as a . . . ", Protein Expr Purif Oct. 2000; 20(1):21–6, abstract only.
Sparks et al, "A simple and rapid procedure for the purification of plasmid DNA . . . ", Anal Biochem Dec. 1983; 135(2):345–8, abstract only.
Santosa, "Rapid extraction and purification of environmental DNA . . . ", Mol Biotechnol Jan. 2001; 17(1):59–64, abstract only.
Ihle et al, "Efficient purification of DNA fragments using . . . ", Nucleic Acids Res Aug. 15, 2000; 28(16):E76, abstract only.
Kahn et al, "Purification of plasmid DNA by tangential . . . ", Biotechnol Bioeng Jul. 5, 2000;69(1):101–6, abstract only.
Ferreira et al, "Anion exchange purification of plasmid DNA . . . ", Bioseparation 2000;9(1);1–6, abstract only.
Madiraju et al, "Development of simple and efficient protocol . . . ", Lett Appl Microbiol Jan. 2000;30(1):38–41, abstract only.

(Continued)

*Primary Examiner*—Anne-Marie Falk
*Assistant Examiner*—Celine Qian
(74) *Attorney, Agent, or Firm*—Nixon & Vanderhye P.C.

(57) ABSTRACT

The present invention provides methods for the purification of plasmid DNA that includes removal of host cell impurities, such as endotoxins, RNA, proteins, and chromosomal DNA, from an aqueous solution containing plasmid DNA and methods for separation and purification of supercoiled plasmid DNA from an aqueous solution containing a mixture of supercoiled and nicked or relaxed plasmid DNA using hydrophobic interaction chromatography supports.

59 Claims, 8 Drawing Sheets

OTHER PUBLICATIONS

Levy et al, "Removal of contaminant nucleic acids by nitrocellulose . . . ", J. Biotechnol Jan. 21, 2000; 76(2–3):197–205, abstract only.

Limor et al, "Contaminant eluted from solid–phase plasmid . . . ", J Biochem Biophys Methods Jul. 28, 1999; 40(1–2):57–64, abstract only.

Ferrus et al, "A rapid procedure for the isolation . . . ", Int Microbiol Jun. 1999;2(2):115–7, abstract only.

Itoh et al, "Automated filtration–based high–throughput . . . ", Genome Res May 1999; 9(5):463–70, abstract only.

Schluep et al, "Purification of plasmids by triplex . . . ", Nucleic Acids Res Oct. 1, 1998;26(19):4524–8, abstract only.

Levison et al, "Recent developments of magnetic beads . . . ", J Chromatogr A Aug. 7, 1998;816(1):107–11, abstract only.

Prazeres et al, "Preparative purification of supercoiled . . .", J Chromatogr A May 8, 1998;806(1):31–45, abstract only.

LaMarr et al, "Large Scale preparation of positively super-coiled . . . ", Nucleic Acids Res Apr. 15, 1997;25(8):1660–1, abstract only.

Itoh et al, "Simple and rapid preparation of plasmid . . . ", Nucleic Acids Res Mar. 15, 1997;25(6):1315–6, abstract only.

Davis et al, "Comparison of plasmid DNA preparation . . . ", Biotechniques Jul. 1996;21(1):92–4, 96–9, abstract only.

Pham et al, "Preparation of pure plasmid or cosmid . . . ", Biotechniques Mar. 1996;20(3):492–7, abstract only.

Ruppert et al, "A filtration method for plasmid . . . ", Anal Biochem Sep 1, 1995;230(1):130–4, abstract only.

Moser et al, "Plasmid and chromosomal DNA . . . ", FEMS Microbiol Lett May 15, 1995;128(3):307–13. abstract only.

Horn et al, "Cancer gene therapy using . . . ", Hum Gene Ther May 1995;6(5):565–73, abstract only.

Wicks et al, "Bacterial lipopolysaccharide . . . ", Hum Gen Ther Mar. 1995;6(3):317–23, abstract only.

Tarczynski et al, "Two–minute miniprep . . . ", Biotechniques Mar. 1994;16(3):514–9, abstract only.

Wang et al, "Large–scale supercoiled plasmid preparation . . . ", Biotechniques Mar. 1994;16(3):460–3.

Feliciello et al, "A modified alkaline lysis method for the . . . ", Anal Biochem Aug. 1, 1993;212(2):394–401.

Chakrabarti et al, "A procedure for large–scale plasmid . . . ", Biotechnol Appl Biochem Oct. 1992;16(2):211–5.

Azad et al, "An improvied method for rapid purification . . . ", Lett Appl Microbiol Jun. 1992;14(6):250–4.

Chandra et al, "Large–scale purification of plasmid DNA . . . ", Anal Biochem May 15, 1992;203(1):169–72.

Cole, "Purification of plasmid and high molecular . . . ", Biotechniques Jul. 1991;11(1):18, 20, 22–4.

He et al, "An improved and rapid procedure . . . ", Genet Anal Tech Appl May 1991;8(3):107–10.

Ishaq et al, "Large–scale isolation of plasmid . . . ", Biotechniques Jul. 1990;9(1):19–20, 22, 24.

McClung et al, "Purification of plasmid DNA by fast protein . . . ", Anal Biochem Mar. 1989;177(2):378–82.

LeBrun et al, "A simple method for the preparation of . . . ", Biotechniques Oct. 1988;6(9):834, 837–8.

Moreau et al, "Purification and separation of various . . . ", Anal Biochem Oct. 1987;166(1):188–93.

Lev, "A procedure for large–scale isolation of RNA . . . ", Analy Biochem Feb. 1, 1987;160(2):332–6.

Gomez–Marquez et al, "A simple procedure for large–scale . . . ", Gene 1987;54(2–3):255–9.

Monstein et al, "A rapid and inexpensive method for . . . ", Biochem Int Jun. 1986;12(6):889–96.

Naumov, "Purification of plasmid DNA by chromatographic methods", Mol Gen Mikrobiol Virusol 1985 Sep.;(9):44–7.

Mukhopadhyay et al, "A simple procedure for large–scale . . . ", Anal Biochem Sep. 1983;133(2):265–70.

Pulleyblank et al, "A method for the purficiation of E.coli . . . ", Mol Biol Rep Aug. 1983;9(3):191–5.

Bachvarov et al, "Large scale purification of plasmid DNA", Prep Biochem 1983;13(2):161–6.

Himmel et al, "Rapid method for purification of plasmid DNA . . . ", J Chromatogr May 7, 1982;240(10:155–63.

Colman et al, "Rapid purification of plasmid . . . ", Eur J Biochem Nov. 2, 1978;91(1):303–10.

Humphreys et al, "A simple method for the preparation . . . ", Biochim Biophys Acta Apr. 2, 1975;383(4):457–63.

Duttweiler et al, "Bacterial growth medium . . . ", Biotechniques Mar. 1998;24(3):438–44.

Best et al, "Purification of supercoiled DNA . . . ", Anal Biochem Jul. 1, 1981;114(2):235–43. (Title Only).

Ugarov et al, "Plasmid purification using hot Mg2+ . . . ", Biotechniques Feb. 1999: 26(2):194–6, 198. (Title Only).

Nicoletti et al, "Optimized PEG method for rapid . . . ", Biotechniues Apr. 1993;14(4):532–4, 536. (Title Only).

Voo et al, "Rapid resuspension of pelleted . . . ", Biotechniques Feb. 1998;24(2):240–3. (Title Only).

Shepard et al. "'Microprep' method for rapidly isolating . . . ", Biotechniques May 1999;26(5):868–70. (Title Only).

Song et al, "Direct lysis method for the . . . ", Anal Biochem Jun. 15, 1999;271(1):89–91. (Title Only).

Yeung et al, "Fast and economical large–scale . . . ", Biotechniques Sep. 1993;15(3):381–2. (Title Only).

Baumann et al, "Large–scale purification . . . "; Biotechniques Dec. 1995;19(6):884–90. (Title Only).

Skingle et al. "An improved method for eliminating . . . ", Biotechniques Sep. 1990:9(3):314, 316–7. (Title Only).

King et al, Isolation of plasmid DNA from . . . , Biotechniques Sep. 1995;19(3):326–30. (Title Only).

Davis et al, "Rapid minipreparation of . . . ", Biotechniques Jan. 1999:26(1):66–8. (Title Only).

Prazeres, et al., Large–scale production of pharmaceutical–grade plasmid DNA for gene therapy: problems and bottlenecks, Trends in Biotechnology, vol. 17, No. 4, (1999), pp. 169–174, XP004162836.

Ferreira, et al., Downstream processing of plasmid DNA of gene therapy and DNA vaccine applications, Trends in Biotechnology, vol. 18, No. 9, (2000), pp. 380–388, XP004214265.

Diogo, et al., Purification of a Cystic Fibrosis Plasmid Vector for Gene Therapy Using Hydrophobic Interaction Chromatography, Biotechnology and Bioengineering. Including: Symposium Biotechnology in Energy Production and Conservation, John Wiley & Sons. New York, US, vol. 68, No. 5, (2000), pp. 576–583, XP002178573.

McLaughlin, et al., Resolution of RNA Using High–Performance Liquid Chromatography, Journal of Chromatography, 418 (1987) 51–72, XP–002112449.

"Scaleable process technology for plasmid DNA production based on hydrophobic interaction chromatography", Presented at The First HIC/RPC Conference, Sep. 26–28, 1999, Phoenix, Arizona.

"Plasmid DNA"presented at Third Annual Meeting of the American Society of Gene Therapy, May 31–Jun. 1, 2000, Denver, Colorado.

"Novel Plasmid DNA Purification Methods Using Hydrophobic Interaction Chromatography", Ram et al, presented at the 20$^{th}$ International Symposium on the Separation and Analysis of Proteins, Peptides and Polynucleotides, Nov. 5–8, 2000, Ljubljana, Slovenia.

"A Novel Technique for the Large–Scale Production of Highly Purified Supercoiled Plasmid DNA by Hydrophobic Interaction Chromatography", Sloane et al, presented at Second Annual Meeting of the American Society of Gene Therapy, Jun. 10–13, 1999, Washington, D.C.

Colote et al., "Analysis and Purification of Plasmid DNA by Reversed–Phase High–Performance Liquid Chromatography", Analytical Biochemistry, 154, 15–20, 1986.

Diogo et al., "Separation and Analysis of Plasmid Denatured Forms Using Hydrophobic Interaction Chromatography", Database HCAPLUS; Analytical Biochemistry, 1999, vol. 275, No. 1, pp 122–124, Abstract.

Onishi et al., "An Assay Method for DNA Topoismerase Activity Based on Separation of Relaxed DNA from Supercoiled DNA Using High–Performance Liquid Chromatography", Analytical Biochemistry, 210, 63–68, 1993.

Green et al., "Purification of Nucleic Acid–Based Pharmaceuticals with Polyflo™ Resin", Clinical Chemistry, Dec. 17–19, 1994, vol. 40, No. 12, p. 2335, Abstract from The 1994 San Diago Conference: The Genetic Revolution.

Weiner et al., "Plasmid purification using reverse–phase high performance liquid chromatography resin PRP", Nucleic Acids Research, Aug. 25, 1988, vol. 16, No. 16p. 8185.

* cited by examiner

Butyl HIC resin bead

Hexyl HIC resin bead

Octyl HIC resin bead

Method for endotoxin removal from plasmid DNA solutions

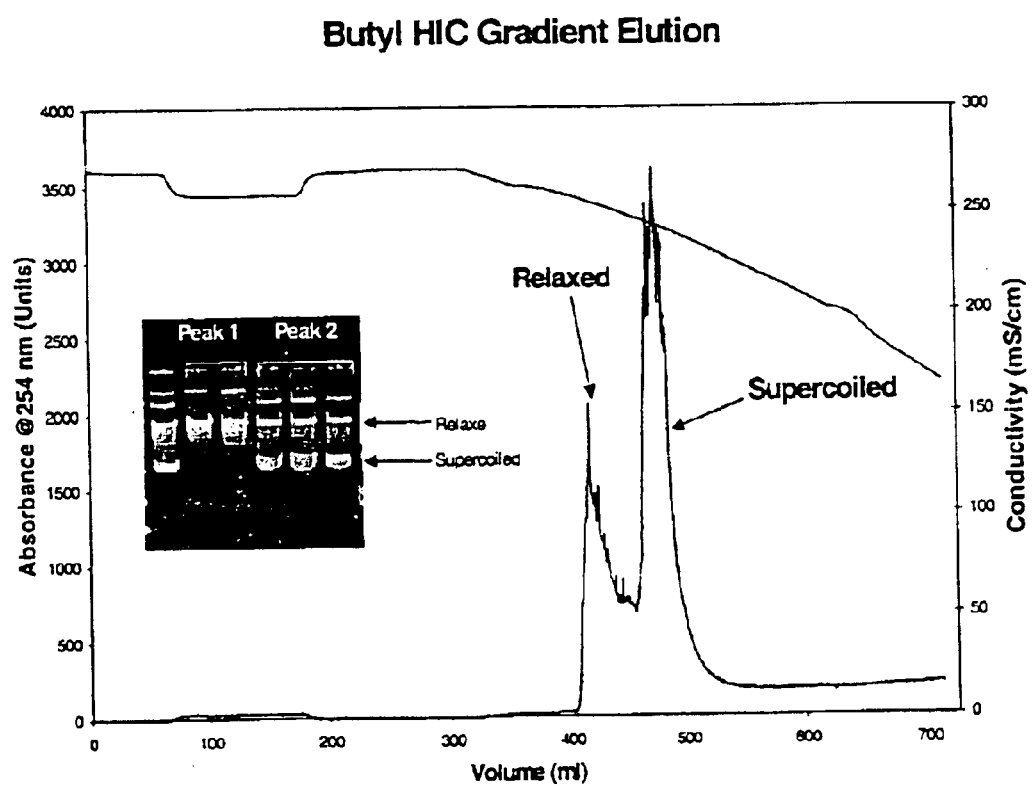
Figure 4 : Chromatogram for the separation of relaxed and supercoiled plasmid DNA using Butyl Hydrophobic Interaction Chromatography – Gradient Elution (Example 5). Inset: Scanned Photograph of Agarose Gel Electrophoresis of samples stained with SYBR Gold Figure 5: Chromatogram for the separation of relaxed and supercoiled plasmid DNA using Butyl Hydrophobic Interaction Chromatography – Gradient Elution – Long column (Example 6). Inset: Scanned Photograph of Agarose Gel Electrophoresis of samples stained with SYBR Gold
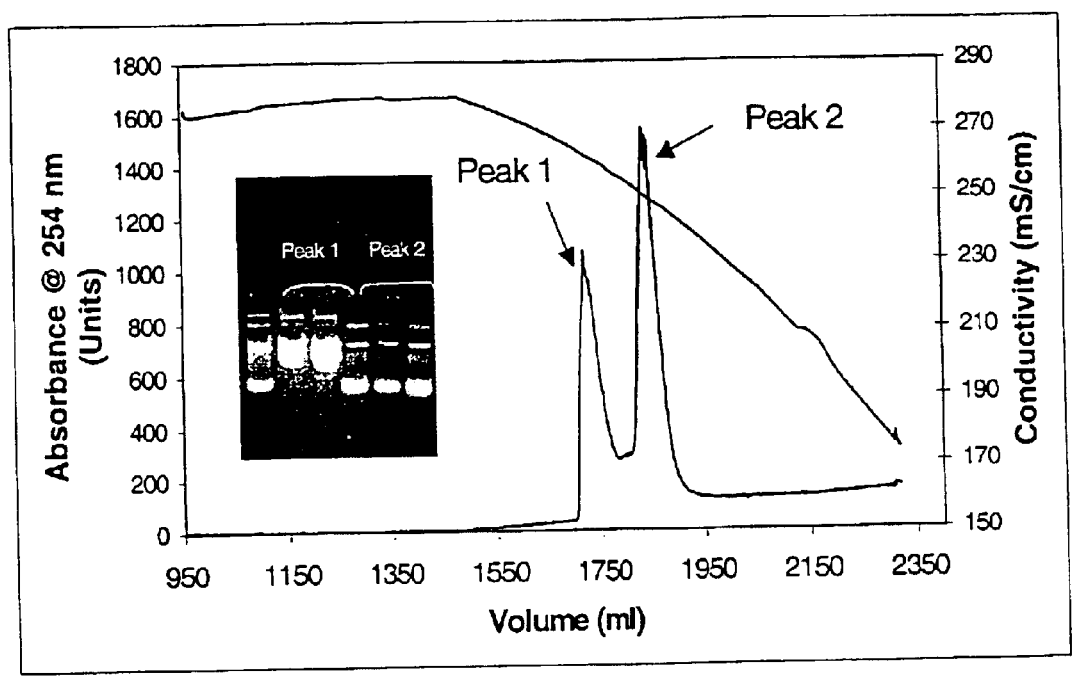

Figure 6: Chromatogram for the separation of relaxed and supercoiled plasmid DNA using Butyl Hydrophobic Interaction Chromatography – Step Elution (Example 7). Inset: Scanned Photograph of Agarose Gel Electrophoresis of samples stained with SYBR Gold
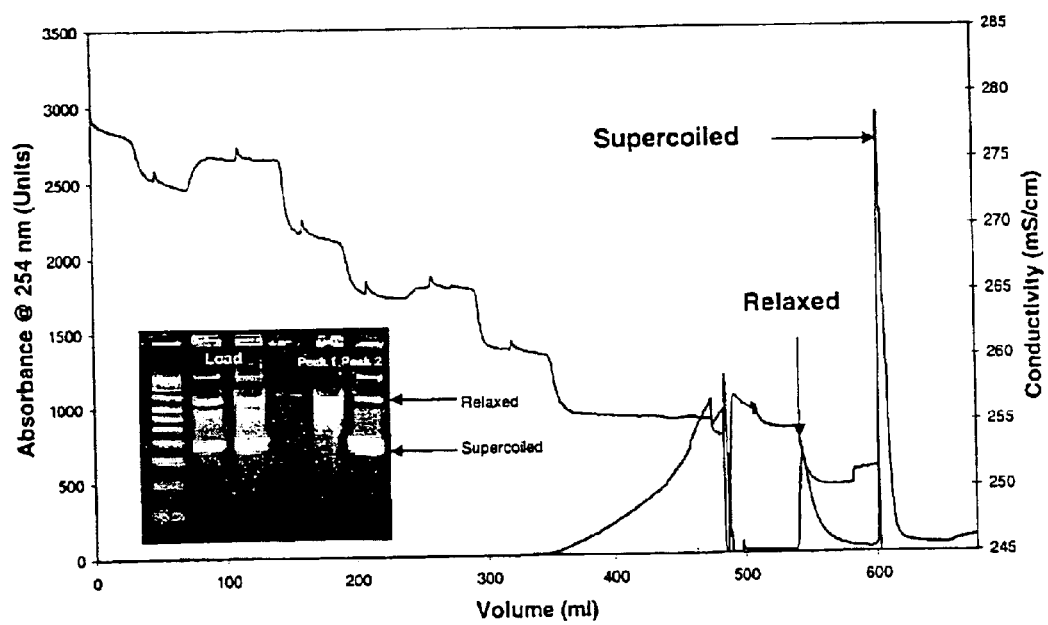

Figure 7: Chromatogram for the separation of relaxed and supercoiled plasmid DNA using Hexyl Hydrophobic Interaction Chromatography – Gradient Elution Long column (Example 8). Inset: Scanned Photograph of Agarose Gel Electrophoresis of samples stained with SYBR Gold
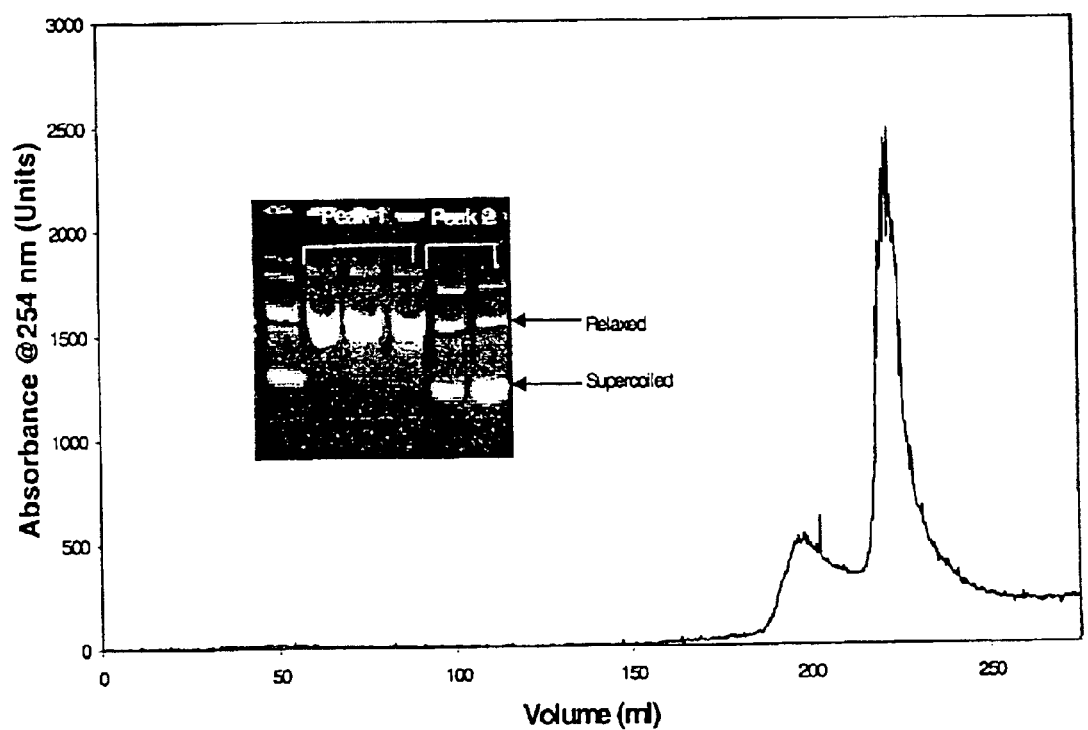

Figure 8: Agarose Gel Electrophoresis of samples SYBR GOLD stained, wherein, from left to right, Lane 1 contains a Marker; Lane 2: Load; Lane 3: Wash 1; Lane 4: Wash 2; Lane 5: Wash 3; Lane 6 : 1M Elution 2; and Lane 7: Water elution
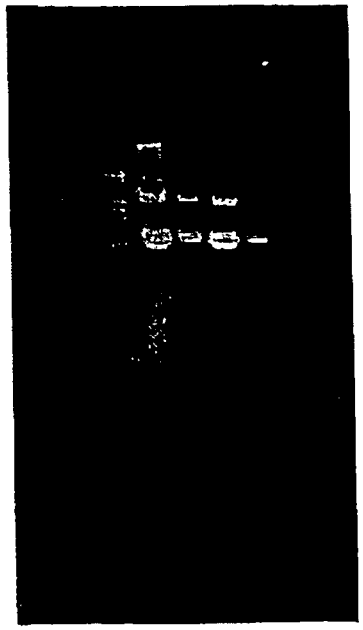

METHODS OF DNA PURIFICATION AND PURIFIED DNA

This application claims benefit of U.S. Provisional Application No. 60/136,772, filed May 28, 1999, the entire contents of which is incorporated herein by reference.

The present invention provides methods for the purification of plasmid DNA that includes removal of host cell impurities, such as endotoxins, RNA, proteins and host cell DNA, from an aqueous solution containing plasmid DNA and methods for separation and purification of supercoiled plasmid DNA from an aqueous solution containing a mixture of supercoiled and nicked or relaxed plasmid DNA using hydrophobic interaction media. Also provided are improved methods for small-scale, such as laboratory or bench-scale, purification of DNA and equipment used in such methods. The present invention provides purified and/or separated DNA, such as plasmid, preferably supercoiled, DNA.

Gene therapy offers a new treatment paradigm for curing human disease. The use of DNA for treatment of genetically caused diseases, including cystic fibrosis, various types of cancer, etc., and immunization against diseases, is a promising mode of therapy that is currently being widely pursued. Rather than altering the disease phenotype by using agents which interact with gene products, or are themselves gene products, gene therapy can theoretically modify specific genes resulting in disease cure or treatment. Gene therapy could also be used as a drug delivery system. To accomplish this, a gene that produces a useful product (RNA, peptide, protein, etc.) or is itself a useful product (such as in the use of antisense DNA) would be inserted into the DNA or cell of a homologous, heterologous or autologous cell of an individual or host cell to be later administered to an individual, either in vivo, ex vivo or in vitro. For example, during blood vessel surgery, a gene that makes an anticlotting factor could be inserted into the DNA of cells lining blood vessels to help prevent dangerous blood clots from forming. Many other conditions might also lend themselves to treatment using this general approach.

Gene therapy is expected to be a powerful tool for treating many of the more than 4,000 known genetic disorders, including cystic fibrosis, heart disease, cancer, arthritis, and other illnesses. Gene therapy generally requires the transfer of genetic material (DNA) into an individual. Gene delivery or the delivery of genetic material can be achieved either by direct administration of gene containing viruses or plasmid DNA to blood or tissues, indirectly through the introduction of cells manipulated in the laboratory to harbor foreign DNA or through various encapsulation or carrier techniques known in the art. Recent reports suggest direct delivery of DNA may also be possible. Several different systems are in use or under consideration for somatic gene transfer. These include, for example, DNA (either naked or complexed), RNA viruses (retroviruses), and DNA viruses (adenovirus, adenoassociated virus [AAV], herpes virus, and poxvirus).

The key advantages of non-viral mode of gene therapy, such as the use of plasmid DNA, is the ease of preparation in large quantities, a great degree of safety, a general lack of integration of the heterologous DNA into the host cell DNA, and the possibility of using gene(s) or gene(s) fragments of virtually unlimited size and number. Further, the use of plasmid DNA in gene therapy does not generally involve the use of extraneous gene(s) or proteins which may induce an unwanted immune response in the recipient. In addition, alternatives to the use of plasmid DNA, such as viral vectors, are relatively more expensive to produce.

Methods currently used to produce plasmid DNA generally provide a mixture of supercoiled plasmid DNA and a nicked (or relaxed) DNA artifact, which is generally not useful in the final application of the plasmid DNA. The methods of the present invention provide a non-destructive separation of supercoiled and nicked plasmid DNA such that while the present methods are exemplified by recovery and use of the supercoiled plasmid DNA, one of ordinary skill will appreciate that either separated form of the plasmid DNA may be considered a useful product of the presently disclosed methods. Moreover, while the present disclosure emphasizes the need for greater purity of supercoiled plasmid DNA in the context of gene therapy, one of ordinary skill in the art will appreciate that plasmid DNA is widely used in recombinant molecular biology beyond the use in gene therapy preparations and the presently disclosed invention finds wide applicability as a preparative method for isolated and purified supercoiled plasmid DNA.

Currently available methods for separation of the two forms of plasmid DNA utilize ion exchange chromatography (A novel, rapid process for purification of plasmids for gene therapy (Bhikhabhai R. Ollivier M. and Blanche F., Amersham Pharmacia Biotech R & D, 75184 Uppsala, Sweeden and RPR Gencell, Rhone-Poulenc Roer, Center de Recherche de Vitry-Alfortville, 13 quai Jules Guesde, 94400 Vitry sur Siene, France. Publication number: 18-1129-51; Preparative purification of supercoiled plasmid DNA using anion exchange chromatography, Duarte Miguel Prazeres, Thomas Schleup, Charles Cooney, Journal of Chromatography A, 606 (1998), 31–45) or size exclusion chromatography (Prazeres, D. M., A comparison of Gel Filtration Chromatographic Supports for Plasmid Purification, Biotechnology Techniques Vol. 11, No. 6, June 1997, p 417–420), coupled with the use of additives such as polyethylene glycol (PEG), detergents, and other components such as hexamine cobalt, spermidine, and polyvinylpyrollidone (PVP). Recently a patent was awarded (Horn, et al (U.S. Pat. No. 5,707,812)) for the purification of supercoiled plasmid DNA using PEG as an additive. However, currently known methods are unable to provide an efficient and cost effective separation of supercoiled and nicked (or relaxed) DNA. In addition, many of the known methods suffer from the disadvantage of using PEG or other additives, which may not be desired in manufacture of plasmid DNA, as they require additional separation, disposal and quality control methods, which can be difficult, more time consuming and more expensive.

Alternative forms of known methods for separation of supercoiled and relaxed forms of plasmid DNA utilize very expensive, proprietary resins, which also utilize solvents, such as acetonitrile, ethanol and other components, like triethylamine and tetrabutyl ammonium phosphate, during processing. These methods are generally not suited for large-scale production due to the use of solvents. Moreover, they cannot be applied to starting materials that have significant amount of relaxed plasmid DNA as the abundant amount of contaminating relaxed plasmid DNA in starting materials tends to reduce the resolution capabilities of these resins. (Green, A. P. et al. Bio. Pharm. Vol. 10, No. 5, pages 52–42, May 1997.)

Additional methods of separating supercoiled and relaxed DNA rely on size-exclusion chromatography, which involves separation of the two forms of plasmid DNA based on the small difference in size. These columns tend to be relatively long, posing significant scale-up problems, making it infeasible to implement in large-scale production. In addition size-exclusion methods need concentrated sample solutions, that are infeasible to obtain with plasmid DNA solutions, due to the highly viscous nature of the DNA. See, A comparison of gel filtration chromatographic supports for plasmid purification G. N. M. Ferreira, J. M. S. Cabral and D. M. F. Prazeres, Biotechnology Techniques, Volume 11, No. 6, June 1997, pp 417–420.

Plasmid DNA preparations, which are produced from bacterial preparations and often contain a mixture of relaxed and supercoiled plasmid DNA, often requires endotoxin removal, as required by the FDA, as endotoxins produced by many bacterial hosts are known to cause inflammatory reactions, such as fever or sepsis in the host receiving the plasmid DNA. These endotoxins are generally lipopolysacchrides, or fragments thereof, that are components of the outer membrane of Gram-negative bacteria, and are present in the DNA preparation as artifacts of the hosts cells or as a part of larger artifacts, such as host cell membranes or macromolecules, used in expression and manufacture of the plasmid DNA for gene therapy, for example. Hence removal of endotoxins is a crucial and necessary step in the purification of plasmid DNA for therapeutic or prophylactic use.

Endotoxin removal from plasmid DNA solutions primarily have used the negatively charged structure of the endotoxins; however plasmid DNA also is negatively charged and hence separation is usually achieved with anion exchange resins which bind both these molecules and, under certain conditions, preferentially elute plasmid DNA while binding the endotoxins. Such a separation results in only partial removal as significant amounts of endotoxins elute with the plasmid DNA and/or a very poor recovery of plasmid DNA is achieved. Other patented methods use detergents, which could pose problems. (Process for the depletion or removal of endotoxins, Coplan, Metin, Moritz, Peter, Schorr, Joachim, U.S. Pat. No. 5,747,663.) In addition, the binding capacity of these resins is only on the order of $10^3$ to $10^4$ EU (endotoxin units)/ml of resin as the resin is occupied by both endotoxin and plasmid DNA, for example, typically requiring 3 to 80 liters of resin, based on reported capacities of 50,000 EU/ml to 2000 EU/ml (Green, A. P. et al. Bio. Pharm. Vol. 10, No. 5, pages 52–62, May 1997. Sterogene technical profile DNA Etox, Sterogene, 5922 Farnsworth Cr., Carlsbad, Calif. 92008).

The present invention provides methods of plasmid DNA separation, isolation and/or purification which may be used in combination or independently. Specifically, the present invention provides methods of separation, purification and/ or isolation of supercoiled and relaxed plasmid DNA as well as methods of separation, purification and/or isolation of plasmid DNA from host cell impurities, such as endotoxin containing components or fragments. Purified, separated and/or isolated plasmid DNA, specifically supercoiled plasmid DNA, compositions are also provided by the present invention. The present invention also provides methods and apparatus for laboratory- or bench-scale separation, isolation and/or purification of plasmid DNA.

The present invention provides methods for isolating desired types of polynucleotides from other components present in mixtures containing these polynucleotides, yielding compositions enriched in the desired type of polynucleotides. The methods include the separation of the polynucleotides from the undesired components by contacting mixtures containing the polynucleotides with hydrophobic interactive media. The separation of the polynucleotides from other components, as well as the separation of types of polynucleotides results from the differing affinities of the polynucleotides and other undesired components for the hydrophobic interactive media under differing ionic conditions. Thus, in the methods of the invention a hydrophobic interactive media is used that has a highly preferential binding for lipopolysaccharides and lipoproteins relative to polynucleotides: this preferential binding occurs over the range of ionic conditions used in the separation process. Also included in the invention are methods that separate supercoiled DNA and relaxed DNA. The methods utilize ionic conditions wherein the supercoiled DNA binds preferentially to the hydrophobic interactive media relative to the relaxed DNA.

It is understood that, when describing a salt concentration used in the methods of this invention, that an equivalent ionic strength of a different salt may be used. It is also understood that, especially with respect to methods which deplete and/or eliminate endotoxin, these methods apply to plasmid as well as non-plasmid DNA.

It is an object of the present invention to provide methods of plasmid DNA separation, isolation and/or purification from contaminating host cell impurities.

It is another object of the present invention to provide methods of separation, purification and/or isolation of plasmid DNA and endotoxin containing components or fragments.

It is yet another object of the present invention to provide methods of separation, purification and/or isolation of supercoiled and relaxed plasmid DNA.

Purified, separated and/or isolated plasmid DNA, specifically supercoiled plasmid DNA, compositions are also provided by the present invention.

In one embodiment, the present invention provides a method of separating endotoxin and other host cell impurities (i.e., RNA, chromosomal DNA, protein) from plasmid DNA involving contacting a cell lysate with a hydrophobic interaction media under conditions where the endotoxin and other contaminating substances bind to the hydrophobic interaction media to form a complex and separating the plasmid DNA and the complex. The endotoxin separated in the method of this embodiment includes endotoxin from Gram-negative microorganisms as well as fragments and cellular and subcellular components bound to these endotoxins and endotoxin fragments. The hydrophobic interaction medium also binds RNA, including t-RNA, r-RNA and m-RNA, host cell proteins and chromosomal DNA. The hydrophobic interaction media useful in the present invention may be in the form of resins, membranes or other support media.

A preferred form of this embodiment includes loading of the mixture of plasmid DNA, with optional other contaminating host cell components, including endotoxin, being present, on a column or bed matrix containing the hydrophobic interaction media, in a manner where the endotoxin and host cell impurities preferentially binds or is retained by the hydrophobic interaction media, and the plasmid DNA is collected as effluent (flow-through) from the loading process or in optional subsequent washing(s) of the hydrophobic interaction media which do not disturb or disrupt the retention of the host cell impurities and endotoxin on and/or in the hydrophobic interaction media. After collection of the plasmid DNA, the column or bed matrix may be regenerated by eluting bound or retained host cell impurities and endotoxin by altering, changing or modifying the hydrophobic interaction conditions of the column or bed by, for example, altering the salt concentration surrounding the column or bed matrix.

Alternate embodiments of the present invention provide methods of separation in the absence of either or both ion exchange chromatography or size exclusion chromatography.

In one preferred form of this embodiment, the column or bed volume is initially equilibrated with an ammonium sulfate reaction solution at a concentration which allows selective binding of the contaminating impurities to the hydrophobic interaction column, preferably, a concentration of about 2M. Salts which may be used in the method of the present invention include mixtures of anions and cations selected from the group consisting of, but not limited to, acetate, phosphate, carbonate, $SO_4^{2-}$, $Cl^-$, $Br^-$, $NO_3^-$, $Mg^{2+}$, $Li^+$, $Na^+$, $K^+$, $NH_4^+$. Mixtures of salts may be used. Moreover, the mixture of plasmid DNA and other contaminating impurities, such as endotoxin, are preferably dialyzed with a dialysis buffer prior to contacting with the column or bed matrix to remove salts and other contaminants which may alter the hydrophobicity of the endotoxin and plasmid DNA and other contaminating impurities, such as endotoxin, in the ammonium sulfate reaction solution. The reaction solution is preferably buffered with, for example, Tris-HCl at a pH in the range of, but not limited to, 6.8 to 8.5, preferably 7.4. Other buffers, are known to those skilled in the art, such as, but not limited to, Tris, TES (N-tris (hydroxymethyl)methyl-2-aminoethane-sulfonic acid), Tricine (N-tris(hydroxymethyl) methylglycine), phosphate, PIPES (Piperazine-N,N'-bis(2-ethane sulfonic acid), MOPS (3-(N-morpholino)-propanesulfonic acid), MES (2-(N-morpholino)-ethanesulfonic acid), MEPES (3-N(N-Morpholino)ethylpiperazine-N'-2-ethanesulfonic acid), and Bicine (N,N-bis(2-hyroxyethyl) glycine) may be used.

The methods of the present invention provide isolated and/or purified plasmid DNA, and a composition containing the plasmid DNA, which has a substantially-reduced endotoxin content, or is endotoxin-free, such that the endotoxin load of the plasmid DNA has been reduced by as much as greater than 95%, preferably, greater than 98%, more preferably greater than 99%, alternatively greater than 99.9% and most preferably greater than 99.99% to 99.999%. The method of the present invention may be used to separate large initial loads of endotoxin, such as at least 200,000 to 400,000 endotoxin units (EU)/milliliter of solution, providing a capacity of at least 600,000 to 3 million EU/ml hydrophobic matrix. Moreover, the process of the present invention provides a product plasmid DNA composition containing a range of less than about 10 to less than about 2500 EU or a range of less than about 1 to less than about 300 EU/mg DNA. Alternatively, the process of the present invention provides a product plasmid DNA composition containing a range of less than about 50 to less than about 1000 endotoxin units (EU) or a range of less than about 10 to less than about 50 EU/mg DNA. The method of the present invention also reduces protein content to less than 0.1% (w/w) RNA to less than 1% (w/w) and chromosomal DNA to less than 1% (w/w).

In another embodiment, the present invention provides a method of separating supercoiled plasmid DNA from relaxed plasmid DNA which includes the steps of contacting a mixture of supercoiled plasmid DNA and relaxed plasmid DNA with a hydrophobic interaction media under a first conditions where both the supercoiled plasmid DNA and the relaxed plasmid DNA bind to the hydrophobic interaction media to form a bound first mixture, altering the first conditions surrounding the bound first mixture to a second conditions to remove the relaxed plasmid DNA from the bound first mixture to form separate components containing a second bound mixture and the relaxed plasmid DNA, and modifying the second conditions surrounding the second bound mixture to a third conditions to remove the supercoiled plasmid DNA from the second bound mixture to form separate components containing the hydrophobic interaction media and the supercoiled plasmid DNA.

In another form of this embodiment, the altering and modifying can be performed by changing the pH conditions of the eluting buffer or solution, in such a way that the relaxed and supercoiled forms could be eluted at different pH conditions, with or without change in salt conditions.

In another form of this embodiment, the altering and modifying can be performed through isocratic elution, where a solution of the same composition, preferably at a salt concentration that can elute both forms of the plasmid DNA, when passed through the column containing the bound plasmid, would sequentially elute the two forms distinctly, in separate fractions.

In another embodiment, the salt conditions and/or other conditions can be modified in such a way that the relaxed form of the plasmid could be collected as the unbound fraction, while the supercoiled form binds to the resin. The supercoiled form can subsequently be eluted by using conditions outlined above.

In another form of this embodiment, the altering and modifying can be performed by use of molecules or a mixture of molecules that competitively bind to the ligands ("displacers") and remove the bound plasmid DNA forms from the matrix as separate components.

In another form of this embodiment, molecules or mixture of molecules that can bind through hydrophobic interaction or otherwise, can be mixed with plasmid DNA solutions, which, on loading on to the column could be sequentially displaced, resulting in separation of the different forms of DNA.

In the above two alternative forms of the embodiment, commonly referred to as "displacement" and "frontal" mode of chromatography, the added molecule may co-elute with the product which, in most cases can be effectively separated using methods known to those in the art.

Displacement chromatography is a mode of chromatography in which two or more molecules bound to a resin are displaced using a displacer molecule that has higher affinity for the resin resulting in sequential displacement and hence elution of the two or more bound molecules. Recently, displacers for hydrophobic interaction resins have been identified, which consists of triblock copolymers including polymethyl methacrylate, acrylic acid, and polydimethylaminoethyl methacrylate (see Ruaan et al "Hydrophobic displacement chromatography of proteins using triblock copolymers as displacers, 1998 AIChE meeting). Other displacers have been successfully developed for displacement chromatography with hydrophobic interaction resins (see Shukla et. al. Hydrophobic displacement chromatography of proteins in 1998 Annual AIChE meeting). Displacers such as 2-(2-butoxyethoxy)ethanol have been used as displacers in reverse phase chromatography, which might be useful.

After binding the two forms of the plasmid, a displacer, such as ones listed above could be used to displace supercoiled and relaxed DNA sequentially from the HIC (hydrophobic interaction column) resins described herein.

In "Frontal" mode of chromatography, the column is loaded with a binary mixture, differing in their affinity for the resin, and upon continually overloading the column, one component displaces the other and results in sequential elution of the two components. In the application of this method for the current invention, the two forms of DNA, for example, could be loaded on a HIC column and overloading of the sample could result in displacement effect leading to the displacement of the relaxed form, which can be collected separately from the supercoiled form.

In one form of this embodiment, the altering and modifying are combined in a continuous process of a gradient elution of the relaxed plasmid DNA and supercoiled plasmid DNA by mixing the bound first mixture with a salt solution, such as ammonium sulfate solution, with a continuously varying concentration of salt, such as ammonium sulfate, the concentration preferably varying from about 3M to about 1 M salt, such as ammonium sulfate. The relaxed plasmid DNA is collected in this form of this embodiment of the invention in a first eluted volume and the supercoiled plasmid DNA is collected in a second eluted volume.

In another preferred form of this embodiment, the supercoiled and relaxed forms of the plasmid DNA are separated by first binding both forms of the DNA to a hydrophobic interaction media in a bed or column at high salt concentrations, or equivalent ionic strengths, such as 2.5 M to 4 M, preferably 3 M, ammonium sulfate, and then eluting, either in a step gradient or continuous gradient manner, the two separate forms of the plasmid DNA off the column, by changing the salt concentration, or equivalent ionic strengths, to a first range of about 2.45 M to about 2.35 M ammonium sulfate and then to a second range of about 0 M (possibly 1 M) to about 2.3 M ammonium sulfate (in the step elution embodiment) or by continuously changing the ammonium sulfate concentration from the range of about 2.5 M to about 4M to a second range of about 0 M (possibly 1 M) to about 2.3 M over a volume of about 1 to about 30 column or bed volumes, preferably at least 6 column or bed volumes (in the continuous gradient embodiment). In each of these forms, the relaxed plasmid DNA elutes from the column or bed media at a salt (ammonium sulfate) concentration in the range of about 2.35 M to about 2.45 M whereas the supercoiled plasmid DNA elutes from the column or bed media at a salt (ammonium sulfate) concentration in the range of about 0M to about 2.3 M.

In another embodiment, the invention provides methods of isolating supercoiled plasmid DNA which includes:
  applying a sample containing supercoiled plasmid to a hydrophobic interaction media under ionic conditions whereby the supercoiled plasmid preferentially binds to the media with respect to non-supercoiled plasmid; and
  adjusting the ionic conditions such that bound supercoiled plasmid is removed from the media.

In another preferred embodiment, the present invention provides a method for the enriching the amount of supercoiled DNA relative to relaxed DNA in a mixture thereof, the method including (1) interacting the mixture containing supercoiled DNA and relaxed DNA with a hydrophobic interactive media containing an alkyl moiety under ionic conditions wherein the supercoiled DNA preferentially binds to the hydrophobic interactive media; (2) treating the hydrophobic interactive media containing the relaxed and supercoiled DNA under ionic conditions that allow the preferential removal of the relaxed DNA; and (3) eluting the supercoiled DNA from the hydrophobic interactive media.

In a further preferred embodiment, the present invention provides a method for removing lipopolysaccharide (LPS) from a composition containing DNA, the method including the steps of (1) interacting the mixture containing the DNA and LPS with a hydrophobic interactive media containing an alkyl moiety, wherein the interacting is under ionic conditions where the LPS preferentially binds to the hydrophobic interactive media relative to the DNA; and (2) treating the hydrophobic interactive media containing the DNA and LPS with ionic conditions that allow the selective removal of the DNA.

The methods of the present invention provide isolated and/or purified supercoiled plasmid DNA, and a composition containing the supercoiled plasmid DNA, which is preferably endotoxin free, such that the amount of supercoiled plasmid DNA present in the composition produced by the presently disclosed methods is at least about 50% by weight of the total plasmid amount to at least about 99% by weight, preferably at least about 60% by weight to at least about 95% by weight, more preferably at least about 70% by weight to at least about 90% by weight, most preferably at least about 75% by weight to at least about 85% by weight, supercoiled plasmid DNA.

Weight percent may be measured, as exemplified herein, by HPLC resolution on a DNA-NPR HPLC column, through a gradient, resulting in peaks with areas corresponding to the amount of each component. The percentage of supercoiled form was calculated as the fraction of the peak area corresponding to supercoiled DNA to the total area of the supercoiled and relaxed plasmid DNA peaks.

Preferred hydrophobic interaction media which may be used in the methods of the present invention include hydrophobic interaction chromatography resins that, for example, contain methacrylate polymer or copolymer backbones, such as methacrylate /ethylene glycol and/or methacrylate/ propylene glycol copolymers (TosoHaas, Montgomeryville, Pa.), and/or an agarose or SEPHAROSE (an agarose based chromatography matrix commercially available from Amersham Biosciences) (Amersham Pharmacia Biotech, Piscataway, N.J.), such as crosslinked or non-crosslinked, agarose, SEPHAROSE, dextran, silica containing polymer, organic polymers (natural or synthetic), a ceramic-containing, or a gel matrix, backbone, or a combination of any of these, with $C_3$ to $C_{10}$ alkyl, branched or straight, pendent side chain ligands. Preferred pendent ligands include propyl, butyl, hexyl and/or octyl ligands. These ligands provide the preferential binding interaction which is exploited in the separation, purification and/or isolation methods of the present invention. One of ordinary skill in the art will appreciate that hydrophobic interaction resins may include ligands in addition to or in place of these alkyl ligands, which will also be useful in the method of the present invention. Examples of such ligands include, but are not limited to, phenyl, octyl, butyl, propyl, neopentyl, hydroxypropyl, benzyl, octadecyl, diphenyl, and methyl as well as substituted and unsubstituted derivatives of same, and combinations thereof. Suitable resin or media materials useful in the present invention include those described, for example, in EP Patent No. 964057, EP Application No. 99109441, JP 2000035423, JP 99127700 and JP 98127665 (Kitamura et al.) the entire contents of each of which are hereby incorporated by reference.

The hydrophobic interaction media may be in the form of beads, which may be packed or loaded into a column or bed reactor, or a crosslinked porous media. The size of bead media may range from 2.5 $\mu$m to greater than or equal to 100 $\mu$m. The size of bead media is preferably in the range of about 30 to about 110 $\mu$m in diameter, such as about 35 to about 100 $\mu$m in diameter, or, alternatively in the range of 35 to 90 $\mu$m in diameter. The hydrophobic interaction media may be present in the form of membranes, such as cellulose or cellulose derivative backbones, polyether sulfones, polysulfones, and derivatives of same and/or other materials known in the filtration and separation arts, including plastics, such as and including, microtiter plates and petri or cell culture dishes and containers.

The beads used in STREAMLINE (Chromatography column, including media available from Amersham Biosciences for expanded bed adsorption separation) columns typically are larger in size with different densities, and are made by various manufactures, including Amersham Pharmacia Biotech, Biosepra Inc, but not limited to these, where the clarified lysate could be flowed through these "expanded bed" columns, resulting in removal of contaminants through binding to the beads that contain the hydrophobic interactive ligands.

Smaller bead sizes, typically are used in high performance separations, including HPLC, where this invention can be utilized to provide a quantitative analytical method for plasmid DNA and/or different forms of DNA.

The beads for the purposes of use in this invention, particularly the separation of two forms of plasmid DNA does not need to be porous as the plasmid DNA is generally too large to be able to occupy the pores, and hence provide any additional capacity. However, for the purposes of contaminant binding, pores could effectively increase capacity as the contaminant molecules such as RNA, protein, endotoxin and DNA fragments are comparable or smaller then the size of pores. In this case porosity will play a role and hence porous resins may be useful.

The methods of the present invention preferably do not require organic solvents, or additives or detergents, such as glycols, polyethylene glycol hexamine cobalt, spermidine or polyvinyl pyrollidone, which would later require separation from the product supercoiled plasmid DNA prior to use in, for example, gene therapy.

BRIEF DESCRIPTION OF THE DRAWINGS

FIG. 4 (insert) shows a scanned image of an agarose gel from Example 5 (butyl HIC) stained with SYBR GOLD (Stain available from Molecular Probes for staining nucleic acids on agarose gels) wherein lane 1 contains a supercoiled DNA Ladder; lanes 2 and 3, contain samples from peak 1 (relaxed) and lanes 3–5 contain samples from peak 2 (supercoiled). (Lanes being numbered from left to right.) The chromatogram from Example 5 of absorbance versus volume shows the separation of relaxed (peak 1) and supercoiled DNA (peak 2).

FIG. 5 (insert) shows a scanned image of an agarose gel from Example 6 (butyl HIC) stained with SYBR GOLD wherein lane 1 contains a marker; lanes 2 and 3 contain samples from peak 1 (relaxed) and lanes 4–6 contain fractions from peak 2 (supercoiled form). (Lanes being numbered from left to right.) The chromatogram from Example 6 shows the separation of relaxed (peak 1) and supercoiled DNA (peak 2) forms.

FIG. 6 (insert) shows a scanned image of an agarose gel from Example 7 wherein lane 1 contains a marker, lanes 2 and 3 contain material loaded on the column; lane 4 contains material from the artifact peak; lane 5 contains material from the 2.4M AS Elution; and lane 6 contains material from the 1M AS Elution. (Lanes being numbered from left to right.) The chromatogram shown separation of relaxed and supercoiled forms of plasmid DNA wherein the artifact peak is a broad first (left) peak, followed to the right by relaxed and supercoiled peaks, respectively.

FIG. 7 (insert) shows a scanned image of an agarose gel from Example 8 (hexyl HIC) wherein lane 1 contains a marker; lanes 2–4 contain material from peak 1 (relaxed form); and lanes 5 and 6 contain fractions from peak 2 (supercoiled form). (Lanes and peaks numbered from left to right.) The chromatogram demonstrates the separation of relaxed from supercoiled forms.

FIG. 8 shows a scanned image of an agarose gel electrophoresis of samples SYBR GOLD stained, from Example 9, wherein lane 1 is a marker; lane 2 contains the material loaded on the column; lanes 3, 4 and 5 contain the washes 1, 2 and 3, respectively; lane 6 contains the 1M elution; and lane 7 contains the water elution.

Figure 1:
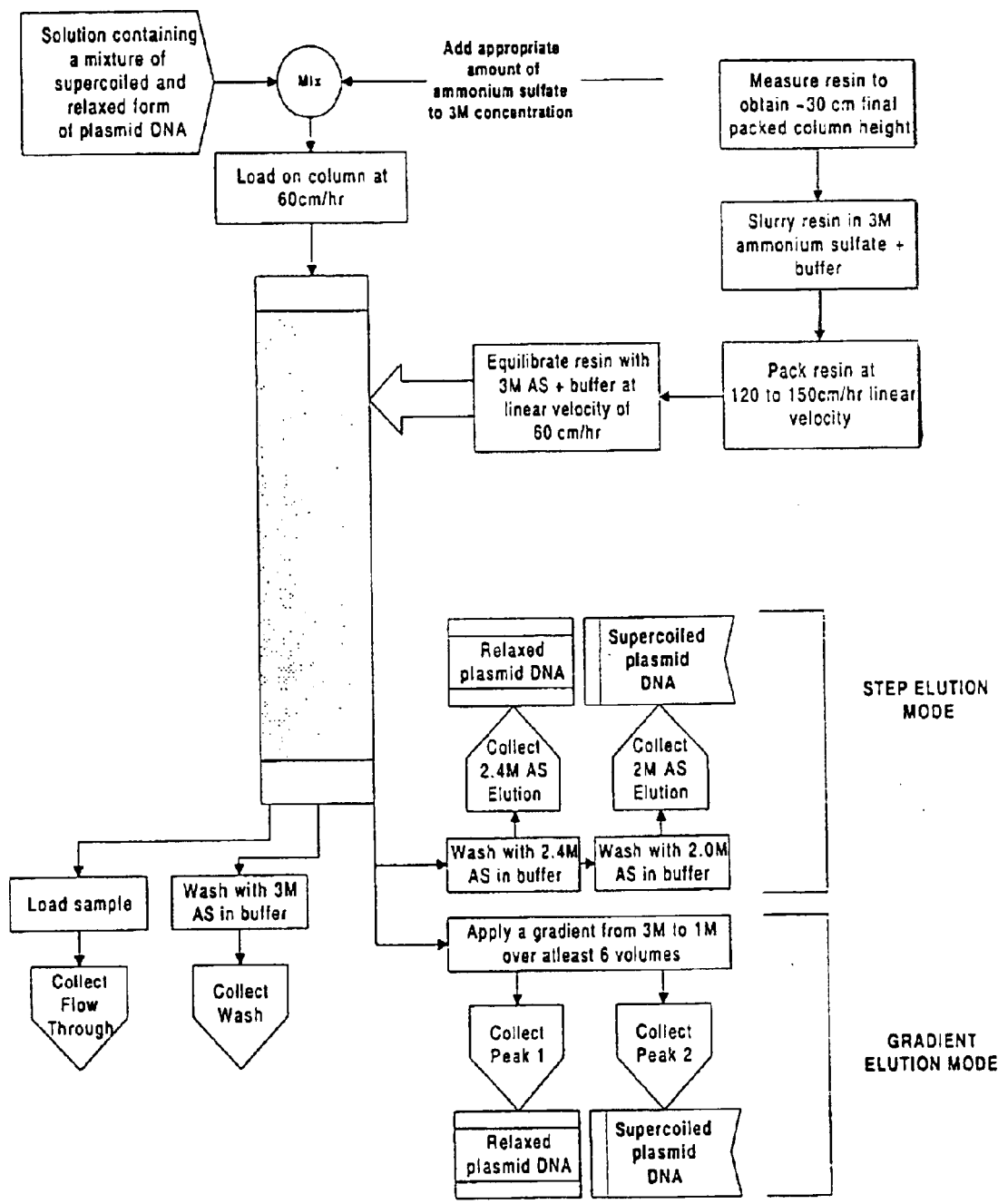
FIG. 1 shows a flow diagram of the various steps involved in performing the exemplified method of separating supercoiled and relaxed plasmid DNA.
Figure 2:
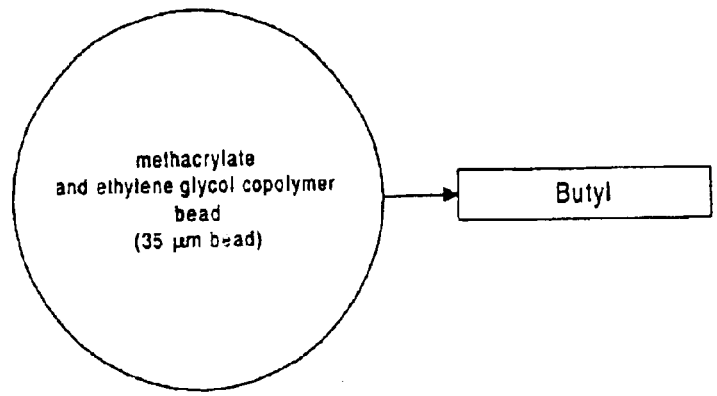
FIG. 2 shows a conceptual depiction of the various hydrophobic interaction supports with the ligand chemistries attached to them that were used in the exemplified method.
Figure 2:
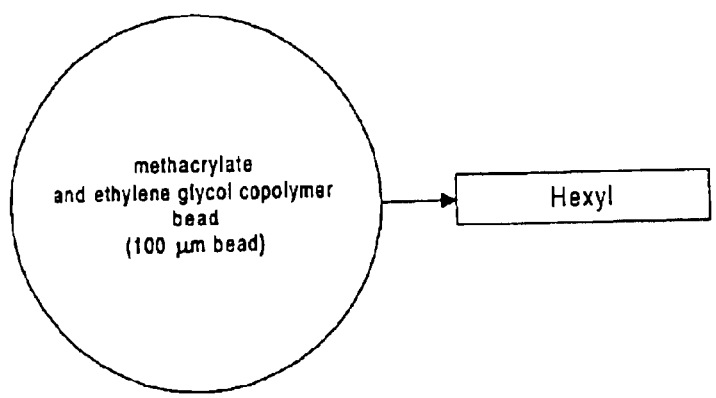
Figure 2:
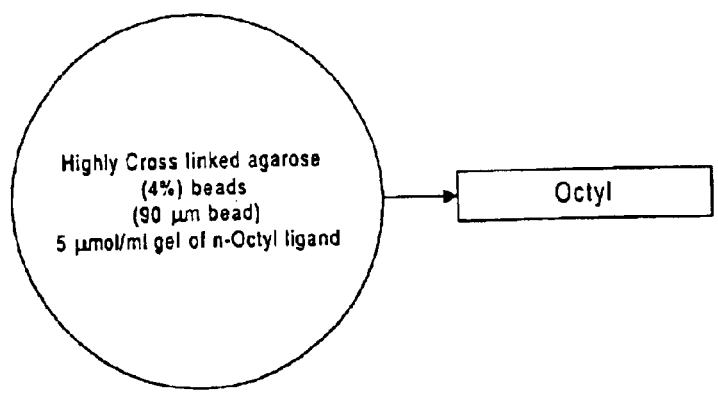
Figure 3:
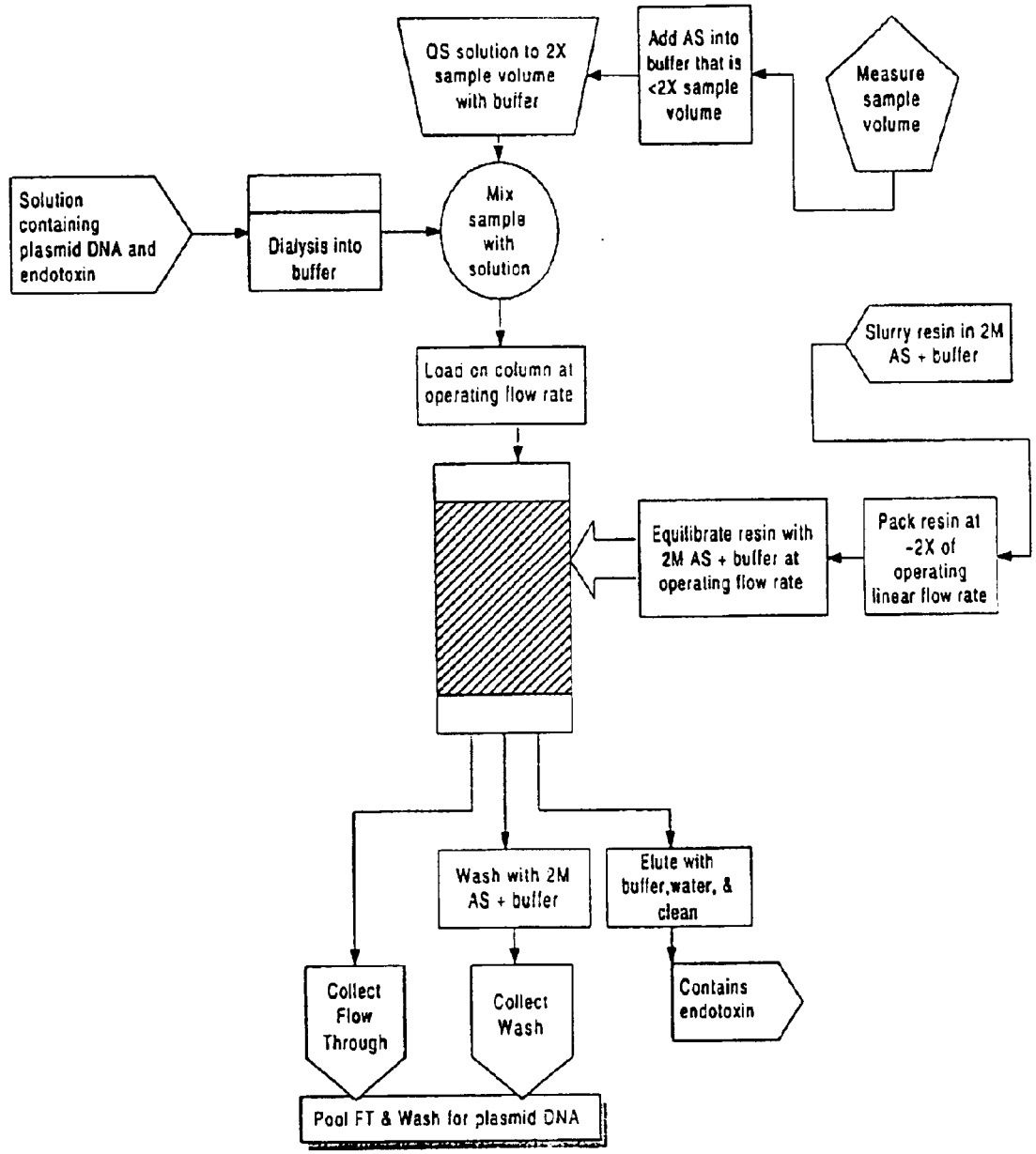
FIG. 3 shows a flow diagram of the various steps involved in performing the exemplified method of separating endotoxin from plasmid DNA.

The methods of the present invention exploits the differences in hydrophobicities of supercoiled plasmid DNA, relaxed plasmid DNA and cellular contaminants, such as endotoxin.

The methods disclosed herein are useful for purifying and isolating supercoiled plasmid DNA, cosmids, and phagemid vectors. These vectors and plasmid DNA could be purified from any source. In addition, plasmid DNA and cosmids present in yeast and mammalian cells can also be purified, as similar mixtures of contaminants, including endotoxins, RNA, proteins and chromosomal DNA, could be present in these preparations. There is also the need to obtain supercoiled form of the plasmid and cosmid DNA from these sources and hence, the methods described herein could be used in purifying DNA in many of these applications.

"Hydrophobic interaction media" is a material comprising (a) a support moiety and (b) a hydrophobic moiety attached either directly or indirectly to the support moiety. Examples of support moieties and hydrophobic moieties are described herein and are known in the art. The hydrophobic moiety provides the basis for preferential binding used in the separation methods described herein. Various examples of "hydrophobic interaction media" are known in the art and are described herein. Other terms used herein also denote hydrophobic interaction media and examples thereof, such as "resin", "matrix", "column", "media", "beads" and "hydrophobic interaction ligand".

"DNA" means any form of deoxyribonucleic acid, including, but not limited to, plasmid (whether supercoiled and/or relaxed or nicked), cosmid, or artificial chromosome.

"Nicked" or "relaxed" DNA means DNA that is not supercoiled. "Supercoiled" DNA is a term well understood in the art.

A "contaminating impurity" is any substance from which it is desired to separate, or isolate, DNA. Contaminating impurities include, but are not limited to, host cell proteins, endotoxin, host cell DNA and/or RNA. It is understood that, what is considered a contaminating impurity can depend on the context in which the methods of the invention are practiced. A "contaminating impurity" may or may not be host cell derived, i.e., it may or may not be a host cell impurity.

"Isolating" or "purifying" a first component (such as DNA) means enrichment of the first component from other components with which the first component is initially found. Extents of desired and/or obtainable purification are provided herein. Preferably, the methods of the invention result in an about five-fold enrichment, preferably an about 10-fold enrichment, preferably an about 20 fold enrichment, preferably an about 50 fold enrichment, preferably an about 100 fold enrichment, preferably an about 200 fold enrichment, preferably an about 500 fold enrichment, preferably an about 1000 fold enrichment. Alternatively, the degree of purification may be expressed as a percentage of the first component with respect to another component, or with respect to the resultant preparation. Examples of such percentages are provided herein.

"Preferential" or "selective" binding or removal of a component means that, for a given condition, the first component binds or is removed to a greater degree with respect to another component.

As would be understood by those skilled in the art, "removal" or "binding" does not necessarily, or even desireably, mean complete, or 100%, removal or binding.

An "aqueous" solution generally indicates a water-based solution (i.e., the main solvent is water), which may or may not be 100% water as solvent.

Isolation of plasmid DNA produced in recombinant bacterial cells involves lysis of the cells and removal of cellular debris, which can be accomplished through various methods. The final solution contains plasmid DNA, typically containing extremely high amounts of endotoxins among other contaminants. The methods of the present invention provides for the removal of significant amounts of the key contaminants, such as RNA, genomic DNA, protein and endotoxin using hydrophobic interaction chromatography as a first step, where the plasmid DNA flows through unbound. A method of the present invention involves, optionally dialyzing the mixed solution obtained from bacterial lysis into a buffer in the pH range of 6.8 to 8.5, preferably a pH of 6.8 to 7.4, containing, preferably, 2M ammonium sulfate, with or without 10mM ethylenediaminetetraaceticacid (EDTA), and flowing the optionally dialyzed solution through a packed chromatography column containing a chromatographic support with a hydrophobic interaction ligand(s), such as any of, or a mixture of, a propyl, a butyl, octyl or hexyl ligand, which had, preferably previously been equilibrated with a buffer in the pH range of 6.8 to 8.5 (preferably 6.8 to 7.4), also containing 2M ammonium sulfate, with or without 10 mM EDTA. The flow-through solution is typically at about a 2M concentration of salts, such as ammonium sulfate, and predominantly contains plasmid DNA (mixture of supercoiled and relaxed) with less than 2% of contaminants. Depending on the variations in the upstream steps, the percentage of supercoiled DNA can range anywhere between 50 and 95% by weight, typically about 75 to 85%, alternatively, 80 to 85%, requiring further purification, involving the removal of the relaxed form of plasmid DNA from the mixture.

Methods of the present invention also make it possible to produce purified plasmid DNA which have endotoxin levels below specified levels, i.e., typically <10 EU/mg plasmid DNA. The methods of endotoxin removal of the present invention are either adaptable to large-scale or small-scale production, enabling economical production of therapeutic and laboratory grade material. These methods exploit the selective binding of endotoxin to the hydrophobic resins described herein which, for large-scale production, may contain capacities exceeding one million units per milliliter of resin used.

Conventionally available methods of endotoxin removal have low capacities (1,000 to 50,000 EU/milliliter of resin) and/or result in low plasmid DNA recoveries and/or involve use of chemical components and/or methods that cannot be readily used in preparation of therapeutic grade material. (U.S. Pat. No. 5,747,663) The method of endotoxin removal of the present invention involves suspending the endotoxin- and plasmid DNA-containing solution in a salt, such as ammonium sulfate or sodium chloride at a concentration of about 2M which makes the endotoxin significantly more hydrophobic than the plasmid DNA and assures binding or preferential interaction and separation of the endotoxin on a resin containing hydrophobic interaction ligands, such as butyl, octyl, and/or hexyl groups, as compared with the plasmid DNA. The salt concentration used may preferably be optimized to bind RNA, protein and endotoxin. A lower salt concentration may be sufficient to provide endotoxin binding alone as endotoxin has a greater affinity for the hydrophobic interaction ligands described herein.

An attractive feature of this method of endotoxin removal is the immense capacity of the resin for the endotoxin, of approximately 1,000,000 EU/ml of resin, in addition to the simplicity and >95% recovery of plasmid DNA. For example, a plasmid DNA solution containing 500 mg of plasmid and 10 million EU of endotoxin can be purified using 10 ml of resin, whereas, at least 1,000 to 4,000 ml of an anion exchange resin would be required for binding the plasmid DNA and the endotoxin, with the added disadvantage of poor recoveries on such an anion exchange resin. The method of the present invention therefore results in savings of 100 to 400 fold in resin cost, and additional savings on column cost and increased recovery of product. The commercially available DNA Etox resin is currently at least 8 fold more expensive than the resins used in the method of the present invention. Another commercial resin (POLY-FLO (Chromatography media available from PureSyn Inc. for plasmid DNA purification)—PureSyn Inc., 87 Great Valley Pkwy Malvern, Pa. 19355) with proprietary chemistry that is useful in endotoxin removal is 5 to 10 fold more expensive and requires the use of solvents and ion-pairing chemicals.

The methods of the present invention provide high quality plasmid DNA comprising greater than 90% supercoiled plasmid DNA from starting material of lesser quality (i.e., a starting material composed of a mixture of relaxed and supercoiled DNA). Additionally, the methods of the present invention are applicable for large-scale processes typically used for production of plasmid DNA for gene therapy. The methods of the present invention enable reliable production of high quality plasmid DNA, independent of variations that typically lead to reduction in quality i.e. generation of relaxed/nicked form of plasmid DNA. These variations could occur during growth of the bacteria producing the plasmid DNA and subsequent isolation and purification steps.

The methods of separating supercoiled and relaxed plasmid DNA, and methods of separating plasmid DNA and endotoxin, of the present invention are based on a discovery that the forms of plasmid DNA and endotoxin exhibit different binding specificities on hydrophobic interaction chromatography resins that, for example, contain $C_4$ to $C_{10}$ alkyl, branched or straight, ligands, and preferably contain either a butyl or hexyl ligand. These ligands provide the preferential binding interaction which is exploited in the separation, purification and/or isolation methods of the present invention. One of ordinary skill in the art will appreciate that hydrophobic resins may include ligands in addition to or in place of these alkyl ligands, which will also be useful in the method of the present invention. Examples of such ligands are also described above. The following non-limiting examples illustrate the methods of the presently disclosed invention. The following general methods were or could be used.

Plasmids for gene therapy applications were extracted from a suitable host bacterium, for example *Escherchia coli*, following fermentation. In the following exemplification of the disclosed invention, *E. coli* STBL-2, which contains plasmid pE1A-K2 was used. Plasmid pE1-A-K2 is a pUC plasmid derivative that contains a suppresser gene from adenovirus Type 5, and contains a kanamycin gene as a selectable marker. Fermentation was conducted aerobically in a suitable yeast extract/glucose medium containing inorganic salts, such as potassium mono basic phosphate, sodium dibasic phosphate, ammonium sulfate and magnesium sulfate at a pH of from 6.5 to 7.8, preferably 7.0, and at a temperature of 37° C. Aeration was set to one volume of air per volume of medium and the agitation set to 800 rpm. Cells were grown in this mode until the glucose was exhausted from the medium, then the DO of the fermentor was controlled by glucose feed and agitation. The feed contained a concentrated solution of glucose (160 µL) and yeast extract (80 g/L) and salts (1.5 g/L ammonium sulfate, $MgSO_4$, 1.5 µL in phosphate buffer). After completion of fermentation, the cells were harvested by centrifugation or by filtration through ultra or microfiltration membranes, and washed with TE (see below) buffer, pH 7.4. Cells were lysed by contacting the suspension with an equal volume of a solution of 0.15N to 0.2N NaOH and 1% sodium dodecyl sulfate (pH 11.5 to 13) with gentle mixing. The alkaline solution was neutralized with a potassium acetate solution. The material was then clarified by either centrifugation or by passing the suspension through a series of depth filters. Plasmid solutions are concentrated by ultrafiltration membranes and diafilered against TE buffer, pH 7. The diafilter retentate can be applied directly to the media described herein.

The plasmid DNA content of the lysate is generally less than 2% of the total nucleic acid with the bulk of the contents being RNA or chromosomal DNA. In addition, the lysate is contaminated with endotoxin and cellular proteins.

The present invention also provides methods of small-, laboratory- or bench-scale production of isolated or purified DNA, and equipment columns and separators useful therein. One of ordinary skill in the art will appreciate that small-scale production of plasmid DNA introduces different challenges, as compared to large-scale production. Specifically, the small-scale separation entails separation of a larger proportion of contaminating RNA in the starting material, such that while the plasmid to RNA ratio in a large-scale starting material may be about 2% (wt/wt), as noted above, the small scale ratio is about 0.1% (wt/wt). Moreover, the culture volume of the small-scale samples are generally about 2 mL to about 2L, as opposed to about 5L to about 1000L in the large-scale separation. The small-scale separations of the present invention involve about 100 µg to about 1 mg of plasmid with a reactor or column bed volume of about 1 to about 20 ml; usually in the range of about 10 ml to about 15 ml. The present invention provides therefore, efficient small-scale production of isolated and/or purified DNA, preferably supercoiled DNA, from impurities, such as endotoxin, RNA and relaxed DNA.

While various procedures are used in the present exemplification, one of ordinary skill will appreciate that other preparative methods and starting materials may be used in the presently disclosed invention.

EXAMPLE 1

Endotoxin Removal Using Butyl Hydrophobic Interaction Chromatography (Small Scale)

E. coli cells harboring the plasmid pE1A-K2 were grown, and lysed using chemical methods, and clarified through filtration methods. All buffers used throughout were filtered through 0.2 µm filter, and samples for endotoxin were stored in polystyrene sample tubes.

A diafiltration retentate (~400 ml) was dialyzed into TE pH 7.4 (50mM Tris, 10mM EDTA adjusted to pH 7.4 with HCl) was used for the experiment. Ammonium sulfate (AS) as required to make the sample 2M was added to 100 ml of TE plus 2M AS, pH 7.4 buffer and partially dissolved. This solution was added to the dialyzed sample to make a final volume of 575 ml, of which 475 ml was used for the experiment.

A Butyl 650S column (Butyl 650S resin from TosoHaas Inc., 156 Keystone Drive, Montgomeryville, Pa. 18936) of 2.6 cm diameter and 15 cm bed height, of approximately 75 ml bed volume was packed and equilibrated with TE buffer, pH 7.4, containing 2M AS. The sample was loaded at a flow rate of 5 ml/min. The flow through was collected, and samples were taken for analysis (DNA concentration, agarose gel, and endotoxin assay. Endotoxin assay was performed with spikes and samples were diluted appropriately to obtain PPC (Positive Product Control) recoveries in the range considered acceptable. Endotoxin concentrations were determined using the BioWhittaker KINETIC-QCL (Endotoxin assay kit available from BioWhittaker) Chromogenic LAL assay as described in BW publication No. P50-650U-5, KINETIC-QCL Test Kit Manual. Following the sample load, TE containing 2M ammonium sulfate was flowed through the column, and collected and sampled. The column was subsequently washed with TE buffer—pH 7.4, USP purified water, and cleaned with 0.5N sodium hydroxide, and rinsed with >15 volumes of USP purified water. Endotoxin was present in each of these washes as shown below in Table 1. In addition to this outstanding endotoxin removal efficiency, significant amount of RNA, protein, and DNA fragments were removed, leaving the sample significantly purified.

TABLE 1

| Sample | DNA conc. (mg/ml) | Endotoxin EU/ml | Total EU units | % Endotoxin | EU per Mg of DNA |
|---|---|---|---|---|---|
| Load | 0.70 | 472,200 | 22,400,000 | 100 | 674,571 |
| Flow through | 0.38 | 1.64 | 771 | 0.003 | 4.31 |
| Wash | 0.56 | 7.48 | 1.196 | 0.005 | 13.42 |

Endotoxin capacity per ml of resin: 3 million EU/ml
Endotoxin reduction in sample: 99.992%

EXAMPLE 2

Endotoxin Removal Using Butyl Hydrophobic Interaction Chromatography (Large Scale)

E. coli cells harboring the plasmid pE1A-K2 was grown, and lysed using chemical methods, and clarified through filtration methods.

The diafiltration retentate (~650 ml) was dialyzed into TE pH 7.4 (50mM Tris, 10mM EDTA adjusted to pH 7.4 with HCl) and ammonium sulfate required to make the sample 2M was added to 1200 ml of TE containing 2M AS, pH 7.4 buffer and dissolved. The volume of this solution was made up to 1300 ml. This solution was added to the dialyzed sample to make a final volume of 1950 ml, and pH was adjusted to 7.4 using HCl.

A Butyl 650S column of 5 cm diameter and 15 cm bed height, of approximately 275 ml bed volume was packed and equilibrated with TE buffer, pH 7.4, containing 2M AS. The sample was loaded at a flow rate of 20 ml/min. The flow through was collected, and samples were taken for analysis (DNA concentration, agarose gel, and endotoxin assay, as described above). Following the sample load, TE containing 2M ammonium sulfate was flowed through the column, and collected and sampled. The column was subsequently washed with TE buffer—pH 7.4, USP purified water, and cleaned with 0.5N sodium hydroxide, and rinsed with >15 volumes of USP purified water. Endotoxin was present in each of these washes as shown below in Table 2. In addition to this extremely outstanding endotoxin removal efficiency, significant amount of RNA, protein, and DNA fragments were removed, leaving the sample significantly purified.

TABLE 2

| Sample | DNA conc. (mg/ml) | Endotoxin EU/ml | Total EU | % Endotoxin | EU per mg of DNA |
|---|---|---|---|---|---|
| Load | 1.59 | 271500 | 176,475,000 | 100 | 170,754 |
| Flowthrough + Wash | 0.34 | <0.5 | 1325 | 0.007 | 1.45 |

Endotoxin capacity per ml of resin: 0.64 million EU/ml
Endotoxin reduction in sample: 99.993%

EXAMPLE 3

Endotoxin removal using Hexyl Hydrophobic Interaction Chromatography (Small Scale)

E. coli cells harboring the plasmid pE1A-K2 was grown, and lysed using chemical methods, and clarified through centrifugation methods. The supernatant was dialyzed into a 20mM potassium phosphate buffer (20 mM potassium phosphate monobasic solution combined with 20 mM potassium phosphate dibasic in a proportion to obtain a pH of 6.8), pH 6.8 and ammonium sulfate required to make the sample 2M was added to 20 ml of KPB (20 mM potassium phosphate buffer) containing 2M AS, pH 6.8 buffer and dissolved. This solution was added to 5 ml of dialyzed sample to make a final volume of 25 ml and pH was adjusted to 6.8.

A Hexyl 650C (TosoHaas) column of 1.6 cm diameter and 4 cm bed height, of approximately 8 ml bed volume was packed and equilibrated with KPB, pH 6.8, containing 2M AS. The sample was loaded at a flow rate of 2 ml/min. The flow through was collected, and samples were taken for analysis (DNA concentration, agarose gel, and endotoxin assay, see above). Following the sample load, KPB containing 2M ammonium sulfate was allowed to flow through the column, collected and sampled. The column was subsequently washed with KPB pH 6.8, USP purified water, and cleaned with 0.5N sodium hydroxide, and rinsed with >15 volumes of USP purified water. Endotoxin was present in each of these washes as shown below in Table 3. In addition to this extremely outstanding endotoxin removal efficiency, significant amount of RNA, protein, and DNA fragments were removed, leaving the sample significantly purified.

TABLE 3

| Sample | DNA conc. (mg/ml) | Endotoxin EU/ml | Total EU units | % Endotoxin | EU per Mg of DNA |
|---|---|---|---|---|---|
| Load | 2.43 | 593500 | 29,675,000 | 100 | 244,238 |
| Flow through + Wash | 0.037 | 0.5 | 35 | 0.0001 | 14 |

Endotoxin capacity per ml of resin: 3.7 million EU/ml
Endotoxin reduction in sample: 99.999%

EXAMPLE 4

Endotoxin Removal Using Octyl Hydrophobic Interaction Chromatography (Small Scale)

E. coli cells harboring the plasmid pE1A-K2 was grown, and lysed using chemical methods, and clarified through centrifugation methods as described above. The supernatant was used for the experiment. Ammonium sulfate required to make the sample 2M was added to 20 ml of TE plus 2M AS, pH 7.4 buffer and dissolved. This solution was added to 10 ml of dialyzed sample to make a final volume of 25 ml and pH was adjusted to 7.4.

An Octyl Sepharose 4 Fast Flow column (Amersham Pharmacia Biotech, Piscataway, N.J.) of 1.0 cm diameter and 10 cm bed height, of approximately 8 ml bed volume was packed and equilibrated with TE, pH 7.4, containing 2M AS. The sample was loaded at a flow rate of 2 ml/min. The flow through was collected, and samples were taken for analysis (DNA concentration, agarose gel, and endotoxin assay). Following the sample load, TE containing 2M ammonium sulfate was flowed through the column, collected and sampled. The column was subsequently washed with TE pH 7.4, USP purified water, and cleaned with 0.5N sodium hydroxide, and rinsed with >15 volumes of USP purified water. Endotoxin was present in each of these washes as shown below in Table 4.

TABLE 4

| Sample | DNA conc. (mg/ml) | Endotoxin EU/ml | Total EU units | % Endotoxin | EU per mg of DNA |
|---|---|---|---|---|---|
| Load | 2.43 | 593500 | 59,350,000 | 100 | 244,238 |
| Flow through + Wash | 0.037 | 32 | 2240 | 0.004 | 280 |

Endotoxin capacity per ml of resin: 7.41 million EU/ml
Endotoxin reduction in sample: 99.996%

EXAMPLE 5

Separation of the Supercoiled and Relaxed Forms of the Plasmid DNA Using Butyl Hydrophobic Interaction Chromatography —Gradient Elution E. coli cells harboring the plasmid pE1A-K2 were grown, and lysed using chemical methods, and clarified through filtration methods, as described above. Gross purification of the plasmid DNA to eliminate major contaminants such as endotoxin, RNA, protein, chromosomal DNA, etc. was performed using butyl hydrophobic interaction chromatography, where, at a concentration of 2M Ammonium sulfate, the plasmid DNA flows through the column while the contaminants bind to the column (see above).

The flow through containing the plasmid DNA was dialyzed and processed on an anion exchange (Bio Sepra) column that did not provide any additional purification. Processing through the Q anion exchange column and diafiltrations are not necessary to achieve the separation on the butyl column. The elution from the Q anion exchange column was diafiltered using a 30 kD regenerated cellulose membrane (0.1 m², Millipore Corporation). The elution from the Q anion exchange column was diafiltered using a 30 kD regenerated cellulose membrane (0.1m², Millipore Corporation). The dialyzed material was adjusted to 3M ammonium sulfate using solid ammonium sulfate.

A Butyl (Toyopearl Butyl 650S—TosoHaas) column of 2.6 cm diameter and approximately 15 cm height was packed at a flow rate of 15–20 ml/min. The column was equilibrated with 3M ammonium sulfate in Tris-EDTA buffer pH 7.4. The sample was loaded at a flow rate of 5 ml/min. The plasmid was bound to the column at 3M ammonium sulfate. The column was then washed with 2–3 column volumes of a 3M ammonium sulfate solution in buffer. The column was then eluted with a gradient of ammonium sulfate concentration from 3M to 1M over 6 bed volumes. During the gradient elution, two peaks resulted, the first peak containing the relaxed form of the plasmid DNA, and the second peak containing the supercoiled form of plasmid DNA as evidenced in agarose gels of fractions (FIG. 4A). The chromatogram is shown in FIG. 4B. The results were further confirmed by an HPLC assay used to determine the percentage of the two forms (Table 5).

Within the limits of sensitivity of the assay, it was confirmed that the second peak contained 85% supercoiled form, whereas the starting material only contained 50–60% supercoiled form. At least 90% of the starting supercoiled plasmid DNA was recovered. The resolution of the peaks were adequate to effect the separation, even with 15 cm column height. This demonstrates the effective separation of supercoiled and relaxed forms of the plasmid using Butyl hydrophobic interaction chromatography. In addition to this excellent separation, residual amount of RNA, protein, and endotoxin could be removed resulting in product that meets the specifications for gene therapy.

TABLE 5

| Sample | % Supercoiled |
| --- | --- |
| Starting material | 63 |
| Peak 1 Fraction | 8 |
| Peak 2 Fraction | 83 |

EXAMPLE 6

Separation of the Supercoiled and Relaxed Forms of the Plasmid DNA Using Butyl Hydrophobic Interaction Chromatography-Gradient Elution Long Column E. coli cells harboring the plasmid pE1A-K2 were grown, and lysed using chemical methods, and clarified through filtration methods, as described above. Gross purification of the plasmid DNA to eliminate major contaminants such as endotoxin, RNA, protein, chromosomal DNA. etc. was performed using butyl hydrophobic interaction chromatography, where, at a concentration of 2M Ammonium sulfate, the plasmid DNA flows through the column while the contaminants bind to the column (see above). The flow through containing the plasmid DNA was dialyzed and processed on an anion exchange column that did not provide any additional purification. The elution from the Q column was diafiltered using a 30kD regenerated cellulose membrane. The dialyzed material was adjusted to 3M ammonium sulfate using solid ammonium sulfate, as described above in Example 5.

A Butyl (Toyopearl Butyl 650S—TosoHaas) column of 2.6 cm diameter and approximately 30 cm height was packed at a flow rate of 15–20 ml/min. The column was equilibrated with 3M ammonium sulfate in Tris-EDTA buffer pH 7.4. The sample was loaded at a flow rate of 5 m/min. The plasmid was bound to the column at 3M ammonium sulfate. The column was then washed with 2–3 bed volumes with a 3M ammonium sulfate buffer solution. The column was then eluted with a gradient of ammonium sulfate concentration from 3M to 1M over 6 bed volumes. During the gradient elution, two peaks resulted, the first peak containing the relaxed form of the plasmid DNA, and the second peak containing the supercoiled form of plasmid DNA as evidenced in agarose gels of fractions (FIG. 5A). The chromatogram is shown in FIG. 5B. The results were further confirmed by an HPLC assay used to determine the percentage of the two forms (Table 6).

Within the limits of sensitivity of the assay, it was confirmed that the second peak contained 90% supercoiled form, whereas the starting material only contained 50% supercoiled form. Baseline resolution of the peaks was obtained with the longer column. This example clearly demonstrates the effective separation of supercoiled and relaxed forms of the plasmid using butyl hydrophobic interaction chromatography. In addition to this excellent separation, residual amounts of RNA, protein, and endotoxin could be removed resulting in product that meets the specifications for gene therapy.

TABLE 6

| Sample | % Supercoiled |
| --- | --- |
| Starting material | 53 |
| Peak 1 Fraction 36 | 15 |
| Peak 2 Fraction 47 | 83 |
| Peak 2 Fraction 49 | 95 |
| Peak 2 Fraction 52 | 91 |

EXAMPLE 7

Separation of the Supercoiled and Relaxed Forms of the Plasmid DNA Using Butyl Hydrophobic Interaction Chromatography—Step Elution Long Column E. coli cells harboring the plasmid pE1A-K2 were grown, and lysed using chemical methods, and clarified through filtration methods, as described above. Gross purification of the plasmid DNA to eliminate major contaminants such as endotoxin, RNA, protein, chromosomal DNA, etc. was performed using butyl hydrophobic interaction chromatography, where, at a concentration of 2M Ammonium sulfate, the plasmid DNA flows through the column while the contaminants bind to the column (see Example 1 above). The flow through and wash were pooled and concentrated using a 30 kD ultrafiltration membrane using tangential flow filtration. The concentrated plasmid DNA was adjusted to 3M ammonium sulfate using solid ammonium sulfate.

A Butyl (Toyopearl Butyl 650S—TosoHaas) column of 1 cm diameter and approximately 30 cm height was packed at a flow rate of 6 ml/min. The column was equilibrated with 3M ammonium sulfate in Tris-EDTA buffer pH 7.4. The sample was loaded at a flow rate of 2 ml/nin. The plasmid was bound to the column at 3M ammonium sulfate. The column was then washed with 2–3 bed volumes with a 3M ammonium sulfate buffer solution. The column was then eluted with various concentrations of ammonium sulfate—2.8M, 2.7M, 2.6M, 2.55M, 2.5M, 2.4M, 1M—using 2–3 column volumes. Peaks were observed in the 2.4M and 1M elutions. Agarose gel electrophoresis of the peaks is shown in FIG. 6A. The gel indicates clear separation of the supercoiled and relaxed forms. The 2.4M elution contains the relaxed form, while the 1M elution contains the supercoiled DNA. The chromatogram is shown in FIG. 6B. The results were further confirmed by an HPLC assay used to determine the percentage of the two forms (Table 7).

Within the limits of sensitivity of the assay, it was confirmed that the second peak contained 93% supercoiled form, whereas the starting material only contained 62% supercoiled form. These results were confirmed by subsequent experiments where 2.3M and 2.2M elutions did not provide the resolution, and the 2.4M elution repeatedly provided significant removal of the relaxed form, thereby enriching for the supercoiled form in the 1M elution. The separation accomplished using step elution is significant in large scale separations, which are more reliably performed using step elutions. This example clearly demonstrates the effective separation of supercoiled and relaxed forms of the plasmid using step elution of butyl hydrophobic interaction chromatography. In addition to this excellent separation, residual amount of RNA, protein, and endotoxin could be removed resulting in product that meets the specifications for gene therapy.

TABLE 7

| Sample | % Supercoiled |
| --- | --- |
| Starting material | 62 |
| 2.4 M Elution | 8 |
| 1 M Elution | 93 |

EXAMPLE 8

Separation of the Supercoiled and Relaxed Forms of the Plasmid DNA Using Hexyl Hydrophobic Interaction Chromatography —Gradient Elution Long Column E. coli cells harboring the plasmid pE1A-K2 were grown, and lysed using chemical methods, and clarified through filtration methods, as described above. Gross purification of the plasmid DNA to eliminate major contaminants such as endotoxin, RNA, protein, chromosomal DNA, etc. was performed using butyl hydrophobic interaction chromatography, where, at a concentration of 2M Ammonium sulfate, the plasmid DNA flows through the column while the contaminants bind to the column (see, for example, Example 1 above). The flow through containing the plasmid DNA was dialyzed and processed on an anion exchange column that did not provide any additional purification. The elution from the Q column was diafiltered using a 30 kD regenerated cellulose membrane. The dialyzed material was adjusted to 3M ammonium sulfate using solid ammonium sulfate (see above).

A Hexyl (Toyopearl Hexyl 650C—TosoHaas) column of 1 cm diameter and approximately 30 cm height was packed at a flow rate of 5 ml/min. The column was equilibrated with 3M ammonium sulfate in Tris-EDTA buffer pH 7.4. The sample was loaded at a flow rate of 2 ml/min. The plasmid was bound to the column at 3M ammonium sulfate. The column was then washed with 2–3 bed volumes with a 3M ammonium sulfate buffer solution. The column was then eluted with a gradient of ammonium sulfate concentration from 3M to 1M over 6 bed volumes. During the gradient elution, two peaks resulted, the first peak containing predominantly the relaxed form of the plasmid DNA, and the second peak containing predominantly the supercoiled form of plasmid DNA as evidenced in agarose gels of fractions (FIG. 7A).

The chromatogram is shown in FIG. 7B. Qualitatively, the second peak contained significantly higher proportion of supercoiled plasmid than the starting material based on agarose gel electrophoresis. Excellent resolution of the peaks were obtained, considering the fact that the bead size was 100 $\mu$m for the Hexyl, compared to 35 $\mu$m for the Butyl.

EXAMPLE 9

Endotoxin Removal Using Butyl Hydrophobic Interaction Chromatography (Using Sodium Chloride)

E. coli cells harboring the plasmid pE1A-K2 was grown, and lysed using chemical methods, and clarified through centrifugation methods. The supernatant was used for the experiment. The sample was purified through an anion exchange column (Q-HYPER D (Anion exchange chromatography media)—BIOSEPRA Inc.). A 2M sodium chloride elution from the column was used for this experiment. The sample was present in 50 mM Tris 10 mM EDTA pH 7.4 buffer with 2M NaCl. A Butyl HIC column (using Butyl 650S resin—TosoHaas) of diameter 1 cm and height 20 cm of approximately 10 ml volume was packed and equilibrated with TE containing 2M sodium chloride. The sample was loaded at a flow rate of 2 ml/min. The flow through was collected, and samples were taken for analysis (DNA concentration, agarose gel, and endotoxin assay). Following the sample load, TE containing 2M ammonium sulfate was flowed through the column, collected and sampled. The column was subsequently washed with TE pH 7.4.

TABLE 8

| Sample | DNA conc. (mg/ml) | Endotoxin EU/ml | Total Eunits EU | % Endotoxin | EU per mg of DNA |
| --- | --- | --- | --- | --- | --- |
| Load | 0.27 | 642 | 16,050 | 100 | 2377 |
| Wash | 0.13 | 5 | 350 | 2 | 38 |

Endotoxin capacity per ml of resin: 1570 EU/ml
Endotoxin reduction in sample: 98%

EXAMPLE 10

Small Scale Plasmid Purification with Butyl Hydrophobic Interaction Chromatography Small-scale plasmid DNA purification is performed using commercially available kits, the most commonly known of which is a Qiagen's Miniprep kit. The methods described herein may be used for purification of plasmid DNA to provide several advantages over commercial kits. The following example demonstrates the use of the hydrophobic interaction chromatography method of the present invention for purification of plasmid DNA on a small scale.

The starting material for purification was obtained through standard methods. Specifically, E. coli cells harboring plasmid of approximately 4.65 Kb size was grown in Luria Broth containing 100 $\mu$g/ml of ampicillin at 37° C. The cells were harvested at an OD of 2.7. The cells were removed from the media through centrifugation. Subsequently, the cell pellet was resuspended in 50 mM Tris-HCl, 10 mM EDTA pH8.0. An equal volume of 200 mm NaOH, 1% SDS solution was added, mixed well and incubated at room temperature for 5 minutes. This step results in lysis of the cells, releasing the cell contents, including plasmid DNA. Neutralization solution consisting of 3.1M potassium acetate (pH 5.5) was added in equal (original) volume and mixed well. The neutralized lysate was then filtered through cheese cloth and filters to remove the precipitate. The clarified lysate was precipitated with 70% isopropanol (adding 2.1 ml isopropanol per 3 ml of clarified lysate). The precipitate was separated through centrifugation and the pellet was washed with 70% ethanol, dried and dissolved in 10mM Tris-HCl, 0.1mM EDTA buffer, pH 8.0. This preparation was frozen at −20° C. until use and was the starting material for the purification experiments.

A Butyl 650S column with a bed volume of 20 ml and bed height of 10 cm was packed in a 1.6 cm diameter column (Pharmacia XK16/20) and equilibrated with 2.2M ammonium sulfate (AS) in 50mM Tris-HCl, 10 mM EDTA (TE) buffer, pH 7.4. The sample for load was prepared by adding solid ammonium sulfate to a final concentration of 2.2M. The sample was diluted with 2.2M AS in Tris-EDTA, pH 7.4 to 10 ml.

Purification conditions were designed to allow the plasmid DNA to be collected in the flow through and the contaminants were bound to the resin.

The sample was loaded at 2 ml/min and flow through was collected. The column was washed with 35 ml of 2.2M AS in TE buffer and collected as Wash 1(10 ml), Wash 2 (14.5 ml), and Wash 3 fractions (10 ml). A peak resulted during the wash. The column was eluted with 55 ml of 1M AS in TE buffer, pH 7.4 and collected as 1M Wash 1 (10 ml) and 1M Wash 2 (45 ml). A peak resulted during 1M AS elution. The column was eluted with 50 ml of USP-Purified Water. A peak resulted. The table below shows the total nucleic acid present in each of the fractions above. The concentrations were calculated based on the absorbance at 260 nm (Conc. ($\mu$g/ml)=A260*50)

TABLE 9

| Column fractions | Conc. ($\mu$g/ml) | Mass ($\mu$g) |
|---|---|---|
| Load | 550.0 | 5503 |
| Wash 1 | 7.6 | 76 |
| Wash 2 | 40.4 | 607 |
| Wash 3 | 5.0 | 50 |
| Wash pool (Plasmid DNA) | 20.9 | 733 |
| 1 M elution | 35.8 | 1611 |
| Water elution | 30.5 | 1523 |

An agarose gel electrophoresis of the samples were preformed. FIG. 8 shows a photocopy of the gel. The photograph of the gel shows the plasmid DNA in the Wash fractions (Lane 3, 4, 5). In comparison with the load sample (Lane 2) no visible RNA is seen in the Wash fractions. The elution fractions contain RNA as seen in Lanes 6 and 7. The endotoxin in the Wash pool was measured using a Kinetic QCL endotoxin assay. No endotoxin was detected in the sample at the sensitivity level of the assay, which was 0.005 EU/ml. The yield of plasmid was 733 $\mu$g from 100 ml of the culture which is similar to that obtainable with commercial kits.

The entire contents of references cited herein and below are incorporated in their entirety by reference.

Production of pharmaceutical-grade plasmid DNA, Magda Marquet, Nancy Horn, Jennifer Meek, Gregg Budahazi, U.S. Pat. No. 5,561,064.

Concentration and size-fractionation of nucleic acids and viruses in porous media, Cole, Kenneth D., U.S. Pat. No. 5,707,850.

Purification of plasmid DNA during column chromatography, Nancy Horn, Greg Budahazi, Magda Marquet, U.S. Pat. No. 5,707,812.

I claim:

1. A method for purifying plasmid DNA from a mixture containing plasmid DNA and at least one host cell impurity comprising the following steps:
    (a) forming a solution comprising a salt with said mixture wherein said solution has a salt concentration in the range of about 2M to 4M to allow selective binding of said at least one host cell impurity to a chromatography support comprising a hydrophobic pendent group;
    (b) contacting said solution containing plasmid DNA with said support at a salt concentration whereby said at least one impurity binds to said hydrophobic pendent group to form a complex; and
    (c) collecting unbound plasmid DNA from said complex without further chromatographic separation;
    wherein said method is conducted in the absence of organic solvents, detergents, glycols, hexamine cobalt, spermidine, and polyvinylpyrollidone.

2. The method of claim 1 wherein the at least one impurity is selected from the group consisting of RNA, endotoxin, chromosomal DNA and protein.

3. The method for claim 1 wherein the at least one impurity is an endotoxin.

4. The method of claim 1 wherein the salt comprises an anion or cation selected from the group consisting of acetate, phosphate, carbonate, $SO_4^{2-}$, $Cl^-$, $Br^-$, $NO_3^-$, $Mg^{2+}$, $Li^+$, $Na^+$, $K^+$ and $NH_4^+$.

5. The method of claim 4 wherein the salt is ammonium sulfate.

6. The method of claim 5 wherein ammonium sulfate is present at a concentration of about 2M.

7. The method of claim 1 wherein the solution comprises sodium salts in a concentration range of about 2M to 4M.

8. The method of claim 7 wherein the sodium salt is sodium chloride.

9. The method of claim 8 wherein the sodium salt is sodium chloride in a concentration of about 2M.

10. The method of claim 1 wherein the pH of the solution has a range of about 6.8 to about 7.4.

11. The method of claim 1 wherein the pH of the solution is about 7.4.

12. The method of claim 1 wherein said pendent groups are selected from the group consisting of $C_3$ to $C_{10}$ alkyl groups and mixtures thereof.

13. The method of claim 1 wherein the support is selected from at least one of a methacrylate polymer and a copolymer backbone and said pendent group is at least one of a propyl, butyl, hexyl, octyl, nonyl, decyl or phenyl group.

14. The method of claim 1 wherein the support is at least one of a methyacrylate ethylene glycol copolymer backbone or a cross-linked agarose backbone.

15. The method of claim 1 wherein the support is in the form of bead in the size range of 15 to 100 $\mu$m.

16. A method of separating supercoiled plasmid DNA from a mixture of supercoiled plasmid DNA and relaxed plasmid DNA and, optionally, at least one host cell impurity comprising the following steps:
    (a) forming a solution by adding a salt to the mixture of supercoiled plasmid DNA and relaxed plasmid DNA and, when present, said at least one host cell impurity;
    (b) contacting the solution with a chromatography support comprising a hydrophobic pendent group at a first salt concentration where both the supercoiled plasmid DNA and relaxed plasmid DNA bind to the hydrophobic pendent group to form a bound first mixture;
    (c) altering the first salt concentration surrounding the bound first mixture to a second salt concentration to remove relaxed plasmid DNA from the bound first mixture to form separate components containing a second bound mixture and relaxed plasmid DNA; and
    (d) modifying the second salt concentration surrounding the said second bound mixture to a third salt concentration to remove supercoiled plasmid DNA from said second bound mixture.

17. The method of claim 16 wherein the at least one host cell impurity is selected from the group consisting of RNA, endotoxin, chromosomal DNA and protein.

18. The method for claim 16 wherein the at least one host cell impurity is an endotoxin.

19. The method of claim 16 wherein said pendent groups are selected from the group consisting of $C_3$ to $C_{10}$ alkyl groups.

20. The method of claim 16 wherein the support is selected from at least one of a methacrylate polymer and a copolymer backbone and said pendent group is at least one of a propyl, butyl, hexyl, octyl, nonyl, decyl or phenyl group.

21. The method of claim 16 wherein the support is at least one of a methyacrylate ethylene glycol copolymer backbone or a cross-linked agarose.

22. A method of claim 16 wherein the support is a resin in the form of beads in the size range of 15 to 100 µm.

23. The method of claim 16 wherein the salt comprises an anion or cation selected from the group consisting of acetate, phosphate, carbonate, $SO_4^{2-}$, $Cl^-$, $Br^-$, $NO_3^-$, $Mg^{2+}$, $Li^+$, $Na^+$, $K^+$ and $NH_4^+$.

24. The method of claim 23 wherein the salt is ammonium sulfate and said first salt concentration is in the range of 2.5M to 4M.

25. The method of claim 16 wherein the first mixture comprises said support equilibrated with a salt solution containing ammonium sulfate which is present in a concentration range of about 2.5M to 4M.

26. The method of claim 16 wherein said altering comprises washing the support with a salt solution containing ammonium sulfate in a concentration of about 2.35M to about 2.45M.

27. The method of claim 16 wherein the modifying comprises washing said second bound mixture with a salt solution containing ammonium sulfate in a concentration of about 1M to 2.3M.

28. The method of claim 16 wherein said altering and said modifying are combined in a continuous process comprising gradient elution of said relaxed plasmid DNA and supercoiled plasmid DNA.

29. The method of claim 16 wherein said separate relaxed plasmid DNA component and said separate supercoiled plasmid DNA are collected and isolated.

30. A method of enriching supercoiled DNA relative to relaxed DNA in a mixture thereof, the method comprising:
    (a) forming a first solution by adding a salt to the mixture of supercoiled DNA and relaxed DNA;
    (b) contacting the first solution with a chromatography support comprising a hydrophobic pendent group at a first salt concentration where both the supercoiled DNA and relaxed DNA bind to the pendent group to form a bound first mixture;
    (c) altering the first salt concentration surrounding the bound first mixture to a second salt concentration to remove relaxed DNA from the bound first mixture to form separate components containing a second bound mixture and relaxed DNA; and
    (d) modifying the second salt concentration surrounding the said second bound mixture to a third salt concentration to remove supercoiled DNA from said second bound mixture to form separate components containing the support and supercoiled DNA.

31. The method of claim 30 wherein said pendent groups are selected from the group consisting of $C_3$ to $C_{10}$ alkyl groups.

32. The method of claim 30 wherein the support is selected from at least one of a methacrylate polymer and a copolymer backbone and said pendent group is at least one of a propyl, butyl, hexyl, octyl, nonyl, decyl or phenyl group.

33. The method of claim 30 wherein the support is at least one of a methyacrylate ethylene glycol copolymer backbone or a cross-linked agarose.

34. A method of claim 30 wherein the support is a resin in the form of beads in the size range of 15 to 100 µm.

35. The method of claim 30 wherein the salt comprises an anion or cation selected from the group consisting of acetate, phosphate, carbonate, $SO_4^{2-}$, $Cl^-$, $Br^-$, $NO_3^-$, $Mg^{2+}$, $Li^+$, $Na^+$, $K^+$ and $NH_4^+$.

36. The method of claim 35 wherein the first solution is ammonium sulfate in a concentration range of 2.5M to 4M.

37. The method of claim 30 wherein the first mixture comprising said support equilibrated with a salt solution containing ammonium sulfate which is present in a concentration range of about 2.5M to 4M.

38. The method of claim 30 wherein said altering comprises washing the support with a salt solution containing ammonium concentration of about 2.35M to about 2.45M.

39. The method of claim 30 wherein the said modifying comprises washing said second bound mixture with a salt solution containing ammonium sulfate in a concentration of about 1M to 2.3M.

40. A method for purifying plasmid DNA from a mixture of same containing plasmid DNA and at least one host cell impurity comprising the following steps:
    (a) forming a first solution comprising a first salt with said mixture wherein said first solution has a salt concentration in the range of about 2M to 4M to allow selective binding of said at least one host cell impurity to a chromatography support comprising a hydrophobic pendent group;
    (b) contacting said first solution containing plasmid DNA with said support at a first salt concentration whereby said at least one impurity binds to said hydrophobic pendent group to form a complex;
    (c) separating unbound plasma DNA from said complex;
    (d) forming a second solution comprising a second salt comprising said unbound plasmid DNA with a second salt concentration, wherein said second salt concentration is different from said first salt concentration;
    (e) contacting said second solution with a chromatography support comprising a hydrophobic pendent group wherein said unbound plasmid DNA binds to said hydrophobic pendent group; and
    (f) collecting supercoiled DNA from said chromatography support of step (e) by altering the salt concentration of said chromatography support of step (e).

41. The method of claim 40 wherein the at least one impurity is selected from the group consisting of RNA, endotoxin, chromosomal DNA and protein.

42. The method for claim 40 wherein the at least one impurity is an endotoxin.

43. The method of claim 40 wherein at least one of the first salt and the second salt comprises an anion or cation selected from the group consisting of acetate, phosphate, carbonate, $SO_4^{2-}$, $Cl^-$, $Br^-$, $NO_3^-$, $Mg^{2+}$, $Li^+$, $Na^+$, $K^+$ and $NH_4^+$.

44. The method of claim 43 wherein at least one of the first salt and the second salt is ammonium sulfate.

45. The method of claim 44 wherein ammonium sulfate is present at a concentration of about 2M.

46. The method of claim 40 wherein at least one of the first solution and the second solution comprises sodium salts in a concentration range of about 2M to 4M.

47. The method of claim 46 wherein the sodium salt is sodium chloride.

48. The method of claim 47 wherein the sodium salt is sodium chloride in a concentration of about 2M.

49. The method of claim 40 wherein the pH of at least one of the first solution and the second solution has a range of about 6.8 to about 7.4.

50. The method of claim 40 wherein the pH of at least one of the first solution and the second solution is about 7.4.

51. The method of claim 40 wherein said pendent groups are selected from the group consisting of $C_3$ to $C_{10}$ alkyl groups and mixtures thereof.

52. The method of claim 40 wherein the support is selected from at least one of a methacrylate polymer and a copolymer backbone and said pendent group is at least one of a propyl, butyl, hexyl, octyl, nonyl, decyl or phenyl group.

53. The method of claim 40 wherein the support is at least one of a methyacrylate ethylene glycol copolymer backbone or a cross-linked agarose backbone.

54. The method of claim 40 wherein the support is in the form of bead in the size range of 15 to 100 µm.

55. The method of claim 28 wherein said continuous process further comprises contacting said first bound mixture with an ammonium sulfate containing salt solution with a continuously varying concentration of ammonium sulfate, said varying concentration ranging from about 3M to about 1M ammonium sulfate, whereby said relaxed plasmid DNA is collected in a first eluted volume and said supercoiled DNA is collected in a second eluted volume.

56. The method of claim 16 further comprising separating said at least one host cell impurity from said supercoiled plasmid DNA and said relaxed plasmid DNA on a separate chromatography support prior to said contacting.

57. The method of claim 56 wherein said separate chromatography support comprises a hydrophobic pendent group.

58. The method of claim 57 wherein said separating comprises chromatographic separation of said at least one host cell impurity at a salt concentration less than said first salt concentration, whereby said at least one host cell impurity binds to said hydrophobic pendent group of said separate chromatography support.

59. The method of claim 30 wherein said altering and said modifying are combined in a continuous process comprising gradient elution of said relaxed plasmid DNA and supercoiled plasmid DNA.

* * * * *